(12) United States Patent
Fairhurst et al.

(10) Patent No.: US 8,188,100 B2
(45) Date of Patent: May 29, 2012

(54) ADENOSINE DERIVATIVES AS A2A RECEPTOR AGONISTS

(75) Inventors: Robin Alec Fairhurst, Horsham (GB); Roger John Taylor, Horsham (GB)

(73) Assignee: Novartis AG, Basel (CH)

( * ) Notice: Subject to any disclaimer, the term of this patent is extended or adjusted under 35 U.S.C. 154(b) by 267 days.

(21) Appl. No.: 12/310,254

(22) PCT Filed: Sep. 13, 2007

(86) PCT No.: PCT/EP2007/059666
§ 371 (c)(1),
(2), (4) Date: Feb. 17, 2009

(87) PCT Pub. No.: WO2008/031875
PCT Pub. Date: Mar. 20, 2008

(65) Prior Publication Data
US 2009/0325967 A1    Dec. 31, 2009

(30) Foreign Application Priority Data

Sep. 14, 2006  (EP) .................................... 06120706

(51) Int. Cl.
*C07D 519/00* (2006.01)
*A61K 31/52* (2006.01)
*A61P 11/00* (2006.01)
*A61P 11/06* (2006.01)
*A61P 37/08* (2006.01)
*A61P 17/06* (2006.01)
*A61P 29/00* (2006.01)
*C07D 473/40* (2006.01)
*C07D 473/16* (2006.01)

(52) U.S. Cl. ..................... 514/263.4; 544/277; 544/264; 536/27.23; 536/27.61

(58) Field of Classification Search .................... 514/46, 514/263.4; 544/277; 536/27.23, 27.61
See application file for complete search history.

(56) References Cited

U.S. PATENT DOCUMENTS

| | | | |
|---|---|---|---|
| 4,008,125 A | 2/1977 | Kurozumi et al. | |
| 4,738,954 A | 4/1988 | Hamilton et al. | |
| 4,873,360 A | 10/1989 | Johnson et al. | |
| 4,954,504 A | 9/1990 | Chen et al. | |
| 5,688,774 A | 11/1997 | Jacobson et al. | |
| 6,307,054 B1 | 10/2001 | Truesdale et al. | |
| 6,376,472 B1 | 4/2002 | Myers et al. | |
| 6,403,567 B1 | 6/2002 | Zablocki et al. | |
| 6,429,315 B1 | 8/2002 | Sledeski et al. | |
| 6,492,348 B1 | 12/2002 | Bays et al. | |
| 6,559,313 B2 | 5/2003 | Myers et al. | |
| 6,677,316 B2 | 1/2004 | Bays et al. | |
| 7,553,823 B2 | 6/2009 | Zablocki et al. | |
| 7,737,126 B2 | 6/2010 | Blatcher et al. | |
| 2003/0092668 A1 | 5/2003 | Liang et al. | |
| 2003/0176390 A1 | 9/2003 | Herling et al. | |
| 2004/0106572 A1 | 6/2004 | Fishman et al. | |
| 2004/0162422 A1 | 8/2004 | Hall et al. | |
| 2005/0101551 A1 | 5/2005 | Sevillano et al. | |
| 2005/0182018 A1 | 8/2005 | Linden et al. | |
| 2006/0142237 A1 | 6/2006 | Fishman et al. | |
| 2006/0189636 A1 | 8/2006 | Critchley et al. | |
| 2007/0099865 A1 | 5/2007 | Fishman et al. | |
| 2007/0191293 A1 | 8/2007 | Langston et al. | |
| 2007/0232626 A1 | 10/2007 | Jacobson et al. | |
| 2008/0027022 A1 | 1/2008 | Linden et al. | |
| 2008/0051364 A1 | 2/2008 | Fishman et al. | |

(Continued)

FOREIGN PATENT DOCUMENTS

EP        0 267 878 A1    5/1988

(Continued)

OTHER PUBLICATIONS

Jacobsen Marlene A "Adenosine receptor agonists" Exp Opin Therapeutic Targets 12(4):489-501 (2002).

(Continued)

*Primary Examiner* — Mark Berch
(74) *Attorney, Agent, or Firm* — Paul D. Strain, Esq.; Strain & Strain PLLC

(57) ABSTRACT

A compound of formula (I), or stereoisomers or pharmaceutically acceptable salts thereof, formula (1), or stereoisomers or pharmaceutically acceptable salts thereof, wherein A, $U^1$, $U^2$, $R^{1a}$, $R^{1b}$, $R^2$ and $R^3$ have the meanings as indicated in the specification, are useful for treating conditions mediated by activation of the adenosine $A_{2A}$ receptor, especially inflammatory or obstructive airways diseases. Pharmaceutical compositions that contain the compounds and a process for preparing the compounds are also described.

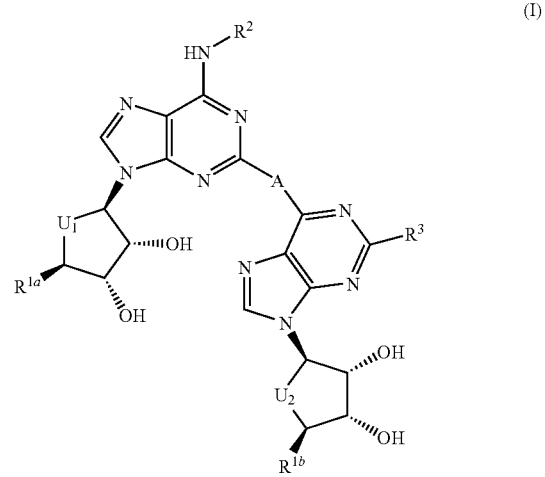

4 Claims, No Drawings

U.S. PATENT DOCUMENTS

| | | | |
|---|---|---|---|
| 2008/0051404 | A1 | 2/2008 | Claiborne et al. |
| 2008/0200483 | A1 | 8/2008 | Fairhurst et al. |
| 2008/0207648 | A1 | 8/2008 | Fairhurst et al. |
| 2008/0214581 | A1 | 9/2008 | Allen et al. |
| 2008/0242683 | A1 | 10/2008 | Fairhurst et al. |
| 2008/0262001 | A1 | 10/2008 | Kranenburg et al. |
| 2008/0300213 | A1 | 12/2008 | Fishman |
| 2008/0312160 | A1 | 12/2008 | Guerrant et al. |
| 2009/0012035 | A1 | 1/2009 | Jacobson et al. |
| 2009/0054476 | A1 | 2/2009 | Goblyos et al. |
| 2009/0081764 | A1 | 3/2009 | Pausch et al. |
| 2009/0093633 | A1 | 4/2009 | Fairhurst et al. |
| 2009/0099214 | A1 | 4/2009 | Fairhurst et al. |
| 2009/0105476 | A1 | 4/2009 | Fairhurst et al. |
| 2009/0123510 | A1 | 5/2009 | Cronstein et al. |
| 2009/0181920 | A1 | 7/2009 | Watkins et al. |
| 2009/0181934 | A1 | 7/2009 | Fairhurst |
| 2009/0240045 | A1 | 9/2009 | Fairhurst et al. |
| 2009/0281126 | A1 | 11/2009 | Fairhurst et al. |
| 2009/0281127 | A1 | 11/2009 | Fairhurst et al. |
| 2010/0041918 | A1 | 2/2010 | Laumen |
| 2010/0190784 | A1* | 7/2010 | Fairhurst et al. .......... 514/232.5 |
| 2010/0197914 | A1 | 8/2010 | Fairhurst |
| 2010/0240680 | A1 | 9/2010 | Fairhurst et al. |
| 2010/0286126 | A1 | 11/2010 | Fairhurst et al. |

FOREIGN PATENT DOCUMENTS

| | | |
|---|---|---|
| JP | 63-219387 | 9/1988 |
| WO | WO 92/05177 A1 | 4/1992 |
| WO | WO 93/22328 A1 | 11/1993 |
| WO | WO 98/50047 | 11/1998 |
| WO | WO 99/67263 A1 | 12/1999 |
| WO | WO 99/67265 A1 | 12/1999 |
| WO | WO 99/67266 A1 | 12/1999 |
| WO | WO 00/23457 A1 | 4/2000 |
| WO | WO 00/78774 A2 | 12/2000 |
| WO | WO 00/78779 A2 | 12/2000 |
| WO | WO 01/60835 A1 | 8/2001 |
| WO | WO 02/22630 A1 | 3/2002 |
| WO | WO 02/055085 A2 | 7/2002 |
| WO | WO 02/070534 A1 | 9/2002 |
| WO | WO 03/029264 A2 | 4/2003 |
| WO | WO 03/086408 A1 | 10/2003 |
| WO | WO 2005/063246 A1 | 7/2005 |
| WO | WO 2005/084653 A2 | 9/2005 |
| WO | WO 2005/107463 A1 | 11/2005 |
| WO | WO 2005/116037 | 12/2005 |
| WO | WO 2006/011130 A1 | 2/2006 |
| WO | WO 2006/045552 A1 | 5/2006 |
| WO | WO 2006/074925 A1 | 7/2006 |
| WO | WO 2006/097260 | 9/2006 |
| WO | WO 2007/121917 A2 | 11/2007 |
| WO | WO 2007/121919 A1 | 11/2007 |
| WO | WO 2007/121920 A2 | 11/2007 |
| WO | WO 2007/121921 A2 | 11/2007 |
| WO | WO 2007/121923 A1 | 11/2007 |
| WO | WO 2007/121924 A2 | 11/2007 |
| WO | WO 2007/147659 A1 | 12/2007 |
| WO | WO 2008/006563 A1 | 1/2008 |

OTHER PUBLICATIONS

International Search Report, PCT/EP2007/059666 (Jan. 18, 2008).
Fairhurst et al., U.S. PTO Office Action, U.S. Appl. No. 12/297,727, Oct. 4, 2010, 13 pgs.
Baraldi et al., "Recent improvements in the field of A3 adenosine receptor ligands", Expert Opinion on Therapeutic Patents, vol. 15, No. 11 (2005), pp. 1507-1519.
Barnard et al., "Inhibition of measles virus replication by 5'-nor carbocyclic adenosine analogues", Antiviral Chemistry & Chemotherapy, vol. 12, No. 4 (2001), pp. 241-250.
Broadley et al., "Drugs Modulating Adenosine Receptors as Potential Therapeutic Agents for Cardiovascular Diseases", Expert Opinion on Therapeutic Patents, vol. 10, No. 11 (2000), pp. 1669-1692.
Cowart et al., "Synthesis of Novel Carbocyclic Adenosine Analogues as Inhibitors of Adenosine Kinase", J. Org. Chem., vol. 64, No. 7 (1999), pp. 2240-2249.
Curran et al., "The Preparation of Optically Active 2, Cyclopenten-1,4-Diol Derivatives from Furfuryl Alcohol", Tetrahedron, vol. 53, No. 6 (1997), pp. 1983-2004.
Duhamel et al., "Acylation Enatioselective D'un Diol, Meso: Le Cis-Cyclopenthen-2 Diol-1,4", Tetrahedron Letters, vol. 26, No. 26 (1985), pp. 3099-3102.
Galkina et al., "Studies on an Oixdative, 1,4-Addition to s-trans-1,3-Dienes, a Key Reaction in a Strigol Total Synthesis", Eur. J. Org. Chem., (2003), pp. 4640-4653.
Ghosh et al. "Synthesis of Enantiomerically Pure 5'-Aza Noraristeromycin Analogs", J. Org. Chem., vol. 60, No. 18 (1995), pp. 5808-5813.
Hegde et al., "5'-Amino-5'-deoxy-5'-noraristeromycin", Chemical Abstracts Index entry for Journal of Organic Chemistry, vol. 63, No. 20 (1998), pp. 7092-7094.
Hegde et al., "5'-Amino-5'-deoxy-5'noraristeromycin", J. Org. Chem., vol. 63, No. 20 (1998), pp. 7092-7094.
Kikugawa et al., "Platelet Aggregation Inhibitors. 6. 12-Thioadenosine Derivatives", Journal of Medicinal Chemistry, vol. 16, No. 12 (1973), pp. 1381-1388.
Marumoto et al., "Synthesis and Coronary Vasodilating Activity of 2-Substituted Adenosines", Chemical and Pharmaceutical Bulletin, vol. 23, No. 4 (1975), pp. 759-774.
Oriyama et al., "Catalytic Asymmetrization of CIS-2-Cyclopentene-1,4-Diol. Highly Efficient and Practical Synthesis . . . ", Heterocycles, vol. 52, No. 3 (2000), pp. 1055-1069.
Palle et al., "Structure-Affinity Relationships of the Affinity of 2-Pyrazolyl Adenosine Analogues for the Adenosine A2A Receptor", Bioorganic & Medicinal Chemistry Letters, vol. 12, No. 20 (2002), pp. 2935-2939.
Silverman J, Rheumatol, vol. 35, No. 4(2008), pp. 1-8.
Terashima et al., "Novel Use of Meso-Compound for the Preparation of Optically Active Compounds . . . ", Tetrahedron Letters, vol. 11 (1977), pp. 1001-1004.
Yang et al., "Amino substituted derivatives of 5'-amino-5'-deoxy-5'-noraristeromycin", Bioorganic & Medicinal Chemistry, vol. 13, No. 3 (2005), pp. 877-882.
Fairhurst, U.S. PTO Office Action, U.S. Appl. No. 11/576,607, Jan. 11, 2010, 39 pgs.
Fairhurst, U.S. PTO Office Action, U.S. Appl. No. 11/576,607, Dec. 23, 2009, 43 pgs.
Fairhurst, U.S. PTO Office Action, U.S. Appl. No. 11/576,607, Jul. 16, 2010, 40 pgs.
Fairhurst, U.S. PTO Office Action, U.S. Appl. No. 11/722,835, Dec. 22, 2009, 37 pgs.
Fairhurst, U.S. PTO Office Action, U.S. Appl. No. 11/722,835, Jul. 16, 2010, 32 pgs.
Fairhurst, U.S. PTO Office Action, U.S. Appl. No. 12/296,714, Jan. 5, 2010, 4 pgs.
Fairhurst, U.S. PTO Office Action, U.S. Appl. No. 12/296,714, May 19, 2010, 63 pgs.
Fairhurst, U.S. PTO Office Action, U.S. Appl. No. 12/296,714, Dec. 23, 2009, 12 pgs.
Fairhurst, U.S. PTO Office Action, U.S. Appl. No. 12/296,714, Dec. 30, 2009, 10 pgs.
Fairhurst, U.S. PTO Office Action, U.S. Appl. No. 12/297,373, Dec. 22, 2009, 8 pgs.
Fairhurst, U.S. PTO Office Action, U.S. Appl. No. 12/297,373, Jul. 15, 2010, 8 pgs.
Fairhurst, U.S. PTO Office Action, U.S. Appl. No. 12/297,404, Dec. 30, 2009, 18 pgs.
Fairhurst, U.S. PTO Office Action, U.S. Appl. No. 12/297,404, Jul. 15, 2010, 38 pgs.
Fairhurst, U.S. PTO Office Action, U.S. Appl. No. 12/297,940, Jan. 22, 2010, 15 pgs.
Fairhurst, U.S. PTO Office Action, U.S. Appl. No. 12/297,007, Dec. 23, 2009, 11 pgs.
Fairhurst, U.S. PTO Office Action, U.S. Appl. No. 12/297,007, Jul. 15, 2010, 32 pgs.
International Search Report, PCT/EP2007/006156, Oct. 12, 2007, 3 pgs.

Kerns et al., "Drug-like Properties: Concepts, Structure Design and Methods: from ADME to Toxicity Optimization", Elsevier (2008), pp. 92-93.

Goosen et al., "Physicochemical Characterization and Solubility Analysis of Thalidomide and Its N-Alkyl Analogs", Pharmaceutical Research, vol. 19, No. 1 (2002), pp. 13-19.

Fourie et al., "Percutaneous delivery of carbamazepine and selected N-alkyl and N-hydroxyalkyl analogues", International Journal of Pharmaceutics, vol. 279, Issues 1-2 (2004), pp. 59-66.

Edwards et al., "Nonpeptidic Inhibitors of Human Neutrophil Elastase. 7. Design, Synthesis, and in Vitro Activity of a Series of Pyridopyrimidine Trifluoromethyl Ketones", J. Med. Chem., vol. 39 (1996), pp. 1112-1124.

Rautio et al., "Piperazinylalkyl prodrugs of naproxen improve in vitro skin permeation", European Journal of Pharmaceutical Sciences, vol. 11 (2000), pp. 157-163.

Pending U.S. Appl. No. 12/297,291, Fairhurst et al., filed Oct. 15, 2008.

Pending U.S. Appl. No. 12/297,491, Fairhurst et al., filed Oct. 17, 2008.

Pending U.S. Appl. No. 13/218,865, Robin Alec Fairhurst et al., filed Aug. 26, 2011.

Pending U.S. Appl. No. 13/218,887, Robin Alec Fairhurst et al., filed Aug. 26, 2011.

Bressi et al., "Adenosine Analogues as Inhibitors of *Trypanosoma brucei* Phosphoglycerate Kinase: Elucidation of a Novel Binding Mode for a 2-Amino-N6-Substituted Adenosine", Journal of Medicinal Chemistry, vol. 43, No. 22 (2000), pp. 4135-4150.

Fairhurst, U.S. PTO Notice of Allowance, U.S. Appl. No. 11/576,607, Jun. 9, 2011, 7 pgs.

Fairhurst, U.S. PTO Notice of Allowance, U.S. Appl. No. 11/722,835, May 27, 2011, 7 pgs.

Fairhurst, U.S. PTO Notice of Allowance, U.S. Appl. No. 12/297,291, Jul. 14, 2011, 9 pgs.

Fairhurst, U.S. PTO Office Action, U.S. Appl. No. 11/576,607, Feb. 17, 2011, 12 pgs.

Fairhurst, U.S. PTO Office Action, U.S. Appl. No. 11/722,835, Jan. 3, 2011, 12 pgs.

Fairhurst, U.S. PTO Office Action, U.S. Appl. No. 12/296,714, Jan. 3, 2011, 16 pgs.

Fairhurst, U.S. PTO Office Action, U.S. Appl. No. 12/296,714, Apr. 28, 2011, 7 pgs.

Fairhurst, U.S. PTO Office Action, U.S. Appl. No. 12/297,291, Mar. 21, 2011, 41 pgs.

Fairhurst, U.S. PTO Office Action, U.S. Appl. No. 12/297,291, Dec. 1, 2010, 21 pgs.

Fairhurst, U.S. PTO Office Action, U.S. Appl. No. 12/297,491, Mar. 24, 2011, 20 pgs.

Fairhurst, U.S. PTO Office Action, U.S. Appl. No. 12/308,637, Feb. 24, 2011, 23 pgs.

Fairhurst, U.S. PTO Office Action, U.S. Appl. No. 12/679,663, Feb. 28, 2011, 21 pgs.

Fairhurst, U.S. PTO Supplemental Notice of Allowance, U.S. Appl. No. 11/576,607, Jun. 15, 2011, 3 pgs.

Ghosh et al., "Synthesis and Biological Evaluation of a Carbocyclic Azanoraristeromycin Siderophore Conjugate", Nucleosides & Nucleotides, vol. 18, No. 2 (1999), pp. 217-225.

Wanner et al., "Synthesis and properties of 2-nitrosoadenosine", J. Chem. Soc., Perkin Trans., vol. 1 (2001), pp. 1908-1915.

Laumen, U.S. PTO Office Action, U.S. Appl. No. 12/312,311, Aug. 9, 2011, 20 pgs.

Siddiqi et al., "Enantiospecific Synthesis of the Fluoro and Epimeric Derivatives of 5'-Noraristeromycin", J. Chem. Soc., Chem. Commun., 1993, pp. 708-709.

Fairhurst, U.S. PTO Restriction Requirement, U.S. Appl. No. 12/247,764, Jul. 15, 2011, 14 pgs.

International Search Report, PCT/EP2008/063869, Jul. 21, 2009, 7 pgs.

Fairhurst, U.S. PTO Notice of Allowance, U.S. Appl. No. 11/722,835, Oct. 21, 2011, 10 pgs.

Fairhurst, U.S. PTO Notice of Allowance, U.S. Appl. No. 12/308,637, Sep. 26, 2011, 13 pgs.

Fairhurst, U.S. PTO Office Action, U.S. Appl. No. 12/297,491, Oct. 12, 2011, 11 pgs.

Fairhurst, U.S. PTO Office Action, U.S. Appl. No. 12/247,764, Oct. 26, 2011, 17 pgs.

Fairhurst, U.S. Notice of Allowance, U.S. Appl. No. 12/297,291, Nov. 10, 2011, 9 pgs.

Fairhurst, U.S. PTO Notice of Allowance, U.S. Appl. No. 11/576,607, Nov. 14, 2011, 9 pgs.

Fairhurst, U.S.PTO Advisory Action, U.S. Appl. No. 12/297,491, Jan. 18, 2012, 15 pgs.

Fairhurst, U.S. PTO Notice of Allowance, U.S. Appl. No. 12/297,491, Feb. 1, 2012, 7 pgs.

Fairhurst, U.S. PTO Office Action, U.S. Appl. No. 13/218,865, Jan. 27, 2012, 21 pgs.

Fairhurst, U.S. PTO Office Action, U.S. Appl. No. 13/218,887, Feb. 1, 2012, 21 pgs.

* cited by examiner

ADENOSINE DERIVATIVES AS A2A RECEPTOR AGONISTS

CROSS-REFERENCE TO RELATED PATENT APPLICATIONS

This application is the National Stage of International Application No. PCT/EP2007/059666, filed Sep. 13, 2007, which is based upon and claims the benefit of priority from prior European Patent Application No. 06120706.4, filed Sep. 14, 2007, the entire contents of all of which are incorporated herein by reference in their entirety.

This invention relates to organic compounds, their preparation and use as pharmaceuticals.

An aspect of the invention provides compounds of formula (I), or stereoisomers or pharmaceutically acceptable salts thereof,

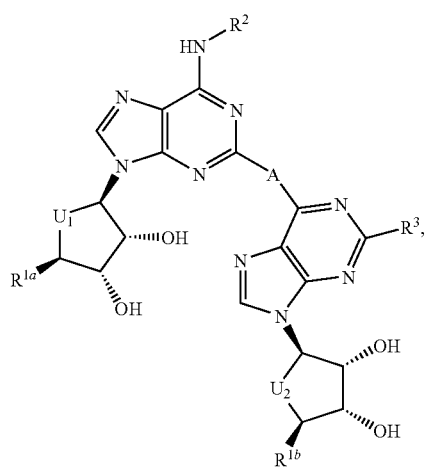

wherein
- $U_1$ and $U_2$ are independently selected from $CH_2$ and O with the proviso that when $U_1$ is O then $R^{1a}$ is not a N-bonded substituent, and when $U_2$ is O then $R^{1b}$ is not a N-bonded substituent;
- $R^1$ and $R^{1b}$ are independently selected from a 3- to 12-membered heterocyclic group containing from 1-4 ring nitrogen atoms and optionally containing from 1-4 other heteroatoms selected from the group consisting of oxygen and sulfur, that group being optionally substituted by oxo, O—$C_1$-$C_8$-alkyl, $C_6$-$C_{10}$-aryl, $R^{1c}$ or by $C_1$-$C_8$-alkyl optionally substituted by OH, or
- $R^1$ and $R^{1b}$ are independently selected from —$NR^4R^4$, $NR^5$—$C_1$-$C_8$-alkylcarbonyl, —$NR^5$—$C_3$-$C_8$-cycloalkylcarbonyl, —$NR^5SO_2$—$C_1$-$C_8$-alkyl, —$NR^5$—$C_7$-$C_{14}$-aralkylcarbonyl and —$NR^5C(=O)$—C(=O)—$NR^5$—$C_1$-$C_8$-alkyl optionally substituted by $R^{1c}$, or
- $R^{1a}$ and $R^{1b}$ are independently selected from $NR^4$—$C_1$-$C_8$-alkyl, $NR^5C(O)C_1$-$C_8$-hydroxyalkyl, $NR^5CO_2C_1$-$C_8$-alkyl, and $NR^5CO_2C_2$-$C_8$-hydroxyalkyl, or
- $R^{1a}$ and $R^{1b}$ are independently selected from $C_1$-$C_8$-hydroxyalkyl, $CH_2$—O—$C_1$-$C_8$-alkyl, $C(O)$—O—$C_1$-$C_8$-alkyl, $C(O)NR^5R^5$ and $C(O)$—NH—$C_1$-$C_8$-alkyl;
- $R^{1c}$ is a 3- or 12-membered heterocyclic ring containing at least one ring heteroatom selected from the group consisting of nitrogen, oxygen and sulfur, said 3- or 12-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl or O—$C_1$-$C_8$-alkyl optionally substituted by aminocarbonyl;
- $R^2$ is $C_1$-$C_8$-alkyl optionally substituted by OH; halogen; $C_6$-$C_{10}$-aryl optionally substituted by OH, $SO_2R^{10}$, $SC_1$-$C_8$-alkyl, CN, halogen, O—$C_7$-$C_{14}$-aralkyl or O—$C_1$-$C_8$-alkyl; a $C_3$-$C_{15}$-carbocyclic group optionally substituted by O—$C_7$-$C_{14}$ aralkyl, $C_3$-$C_{15}$-carbocyclic group, O—$C_1$-$C_8$-alkyl, $C_2$-$C_8$-alkenyl, $C_2$-$C_8$-alkynyl or $C_1$-$C_8$-alkyl; O—$C_1$-$C_8$-alkyl; —$SO_2$—$C_1$-$C_8$-alkyl; a 3- to 12-membered heterocyclic group containing from 1-4 ring nitrogen atoms and optionally containing from 1-4 other heteroatoms selected from the group consisting of oxygen and sulfur, that group being optionally substituted by a 3- to 12-membered heterocyclic group containing from 1-4 ring nitrogen atoms and optionally containing from 1-4 other heteroatoms selected from the group consisting of oxygen and sulfur, $C_7$-$C_{14}$-aralkyl or $C_6$-$C_{14}$-aryl optionally substituted by O—$C_7$-$C_{14}$-aralkyl; or
- $R^2$ is $C_3$-$C_{15}$-carbocyclic group optionally substituted by O—$C_7$-$C_{14}$-aralkyl, $C_3$-$C_{15}$-carbocyclic group, O—$C_1$-$C_8$-alkyl, or $C_1$-$C_8$-alkyl; or
- $R^2$ is a 3- to 12-membered heterocyclic group containing from 1-4 ring nitrogen atoms and optionally containing from 1-4 other heteroatoms selected from the group consisting of oxygen and sulfur, that group being optionally substituted by 3- to 12-membered heterocyclic group containing from 1-4 ring nitrogen atoms and optionally containing from 1-4 other heteroatoms selected from the group consisting of oxygen and sulfur, $C_7$-$C_{14}$-aralkyl, or $C_6$-$C_{14}$-aryl optionally substituted by O—$C_7$-$C_{14}$-aralkyl;
- $R^3$ is hydrogen, halo, $C_2$-$C_8$-alkenyl, $C_2$-$C_8$-alkynyl or $C_1$-$C_8$-alkoxycarbonyl, or
- $R^3$ is amino optionally substituted by $C_3$-$C_8$-cycloalkyl optionally substituted by amino, hydroxy, $C_7$-$C_{14}$-aralkyloxy, —$SO_2$—$C_6$-$C_{10}$-aryl or —NH—C(=O)—NH—$R^{3c}$, or
- $R^3$ is amino substituted by $R^{3a}$, —$R^{3a}$—$C_7$-$C_{14}$-aralkyl or a $C_5$-$C_{15}$-carbocyclic group optionally substituted by OH, $C_1$-$C_8$-alkyl or $C_1$-$C_8$-alkoxycarbonyl, or
- $R^3$ is aminocarbonyl optionally substituted by $R^{3b}$, or
- $R^3$ is $C_1$-$C_8$-alkylamino optionally substituted by OH, $R^{3b}$, amino, di($C_1$-$C_8$-alkyl)amino, —NH—C(=O)—$C_1$-$C_8$-alkyl, —NH—$SO_2$—$C_1$-$C_8$-alkyl, —NH—C(=O)—NH—$R^{3c}$, —NH—C(=O)—NH—$C_1$-$C_8$-alkyl-$R^{3b}$, a $C_5$-$C_{15}$-carbocyclic group or by $C_6$-$C_{10}$-aryl optionally substituted by $C_6$-$C_{10}$-aryloxy, or
- $R^3$ is $C_1$-$C_8$-alkylaminocarbonyl or $C_3$-$C_8$-cycloalkylamino-carbonyl optionally substituted by amino, $C_1$-$C_8$-alkylamino, di($C_1$-$C_8$-alkyl)amino or —NH—C(=O)—NH—$R^{3d}$, or
- $R^3$ is a 3- to 12-membered heterocyclic group containing from 1-4 ring nitrogen atoms and optionally containing from 1-4 other heteroatoms selected from the group consisting of oxygen and sulfur, that group being optionally substituted by 0-3$R^4$;
- $R^{3a}$ and $R^{3b}$ are each independently a 3- to 12-membered heterocyclic group containing at least one ring heteroatom selected from the group consisting of nitrogen, oxygen and sulfur; optionally substituted by halo, cyano, oxo, OH, carboxy, nitro, $C_1$-$C_8$-alkyl, $C_1$-$C_8$-alkylcarbonyl, OH—$C_1$-$C_8$-alkyl, $C_1$-$C_8$-haloalkyl, amino-$C_1$-$C_8$-alkyl, amino(OH)$C_1$-$C_8$-alkyl or $C_1$-$C_8$-alkoxy optionally substituted by aminocarbonyl;

$R^{3c}$ is a 5 or 6-membered heterocyclic group containing at least one ring heteroatom selected from the group consisting of nitrogen, oxygen and sulfur, which is optionally substituted by a 5- or 6-membered heterocyclic group containing at least one ring heteroatom selected from the group consisting of nitrogen, oxygen and sulfur;

$R^{3d}$ are independently a 5- or 6-membered heterocyclic ring containing at least one ring heteroatom selected from the group consisting of nitrogen, oxygen and sulfur, said 5- or 6-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl, $C_1$-$C_8$-alkoxy optionally substituted by aminocarbonyl, or a 5- or 6-membered heterocyclic ring containing at least one ring heteroatom selected from the group consisting of nitrogen, oxygen and sulfur, said ring also being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl, or $C_1$-$C_8$-alkoxy optionally substituted by aminocarbonyl;

$R^4$ is selected from OH, $C_1$-$C_8$-alkyl optionally substituted by OH, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl or -halogen, O—$C_6$-$C_{10}$-aryl optionally substituted by OH, $C_1$-$C_8$-alkyl, O—$C_1$-$C_8$-alkyl or -halogen, $NR^{4a}R^{4b}$, $NHC(O)R^{4c}$, $NHS(O)_2R^{4d}$, $NHS(O)_2R^{4e}$, $NR^{4f}C(O)NR^{4e}R^{4h}$, $NR^{4f}C(O)NR^{4g}R^{4h}$, $NR^{4i}C(O)OR^{4j}$, $C_1$-$C_8$-alkylcarbonyl, $C_1$-$C_8$-alkoxycarbonyl, di($C_1$-$C_8$-alkyl)aminocarbonyl, $COOR^{4k}$, $C(O)R^{4l}$, $NHC(O)R^{4q}$, $NHC(=NR^{4m})N(R^{4n})R^{4o}$, and a 3- to 12-membered heterocyclic group containing at least one ring heteroatom selected from the group consisting of nitrogen, oxygen and sulfur optionally substituted by $COOR^{4p}$;

$R^{4a}$, $R^{4c}$, $R^{4f}$, $R^{4h}$ and $R^{4i}$ are, independently, H, or $C_1$-$C_8$-alkyl;

$R^{4b}$ is H, $C_1$-$C_8$-alkyl a 3- to 12-membered heterocyclic group containing at least one ring heteroatom selected from the group consisting of nitrogen, oxygen and sulfur, optionally substituted by 0-3$R^5$ or $C_6$-$C_{10}$-aryl;

$R^{4d}$, $R^{4e}$, and $R^{4j}$ are, independently, $C_1$-$C_8$-alkyl or a 3- to 12-membered heterocyclic group containing at least one ring heteroatom selected from the group consisting of nitrogen, oxygen and sulfur, optionally substituted by 0-3$R^5$;

$R^{4g}$ is $C_1$-$C_8$-alkyl optionally substituted by a 3- to 12-membered heterocyclic group containing at least one ring heteroatom selected from the group consisting of nitrogen, oxygen and sulfur, optionally substituted with $SO_2R^{10}$, CN, or 0-3$R^5$, or $R^{4g}$ is a $C_6$-$C_{10}$-aryl optionally substituted by OH, $C_1$-$C_8$-alkyl, O—$C_1$-$C_8$-alkyl, $SO_2R^{10}$ or -halogen, or $R^{4g}$ is a $C_7$-$C_{14}$-aralkyl optionally substituted by OH, O—$C_1$-$C_8$-alkyl, halogen, $C_6$-$C_{10}$-aryl, $SO_2R^{10}$, CN, —C(=NH)NH2, or O—$C_6$-$C_{10}$-aryl, or $R^{4g}$ is a 3- to 12-membered heterocyclic group containing at least one ring heteroatom selected from the group consisting of nitrogen, oxygen and sulfur, optionally substituted by 0-3$R^5$;

$R^{4k}$ is H, $C_1$-$C_8$-alkyl, $C_6$-$C_{10}$-aryl or a 3 to 12-membered heterocyclic group containing at least one ring heteroatom selected from the group consisting of nitrogen, oxygen and sulfur;

$R^{4l}$ is $C_1$-$C_8$-alkyl, $C_6$-$C_{10}$-aryl, $NHR^6$ or a 3- to 12-membered heterocyclic group containing at least one ring heteroatom selected from the group consisting of nitrogen, oxygen and sulfur;

$R^{4m}$ is CN;

$R^{4n}$ is H or $C_1$-$C_8$-alkyl;

$R^{4o}$ is H, $C_1$-$C_8$-alkyl optionally substituted by OH or by a 3- to 12-membered heterocyclic group containing at least one ring heteroatom selected from the group consisting of nitrogen, oxygen and sulfur, optionally substituted with $SO_2R^{10}$, CN, or 0-3$R^5$, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl $SO_2R^{10}$ or -halogen;

$R^{4p}$ is H, $C_1$-$C_8$-alkyl or $C_7$-$C_{14}$-aralkyl;

$R^{4q}$ is $C_6$-$C_{10}$-aryl optionally substituted by OH, C(=NH)$NH_2$, or $SO_2NH_2$, or a 3- to 12-membered heterocyclic group containing at least one ring heteroatom selected from the group consisting of nitrogen, oxygen and sulfur optionally substituted by 0-3$R^5$ or a 3- to 12-membered heterocyclic group containing at least one ring heteroatom selected from the group consisting of nitrogen, oxygen and sulfur, optionally substituted by 0-3$R^5$;

$R^5$ is selected from OH, $C_1$-$C_8$-alkyl optionally substituted by OH, CN, $SO_2R^{10}$ or halogen, $C_7$-$C_{14}$-aralkyl optionally substituted with OH, O—$C_1$-$C_8$-alkyl, $C_6$-$C_{10}$-aryl, or O—$C_5$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl or -halogen, O—$C_6$-$C_{10}$-aryl optionally substituted by OH, $C_1$-$C_8$-alkyl, O—$C_1$-$C_8$-alkyl optionally substituted by halogen, $NR^{5a}R^{5b}$, $NHC(O)R^{5c}$, $NHS(O)_2R^{5d}$, $NHS(O)_2R^{5e}$, $NR^{5f}C(O)NR^{5g}R^{5h}$, $NR^{5i}C(O)OR^{5j}$, $C_1$-$C_8$-alkylcarbonyl, $C_1$-$C_8$-alkoxycarbonyl, di($C_1$-$C_8$-alkyl)aminocarbonyl, $COOR^{5k}$, $C(O)R^{5l}$, a C(O)—$C_6$-$C_{10}$-aryl optionally substituted by OH, —COOH, $C_1$-$C_8$-alkyl, O—$C_1$-$C_8$-alkyl, -halogen, or $SO_2R^{10}$, $C(O)NHR^{5m}$ or a 3-12-membered heterocyclic group containing at least one ring heteroatom selected from the group consisting of nitrogen, oxygen and sulfur, optionally substituted by 0-3$R^7$;

$R^{5a}$, $R^{5b}$, $R^{5c}$, $R^{5f}$, $R^{5h}$ and $R^{5i}$ are, independently, H, $C_1$-$C_8$-alkyl or $C_6$-$C_{10}$-aryl;

$R^{5d}$, $R^{5e}$, $R^{5g}$, $R^{5l}$ and $R^{5m}$ are, independently, $C_1$-$C_8$-alkyl or a 3- to 12-membered heterocyclic group containing at least one ring heteroatom selected from the group consisting of nitrogen, oxygen and sulfur, optionally substituted by $COOR^8$;

$R^{5k}$ is H, $C_1$-$C_8$-alkyl, $C_6$-$C_{10}$-aryl or a 3- to 12-membered heterocyclic group containing at least one ring heteroatom selected from the group consisting of nitrogen, oxygen and sulfur;

$R^{5l}$ is $C_1$-$C_8$-alkyl, $C_6$-$C_{10}$-aryl or a 3- to 12-membered heterocyclic group containing at least one ring heteroatom selected from the group consisting of nitrogen, oxygen and sulfur, optionally substituted by $COOR^9$;

$R^6$ is $COOR^{6a}$ or a 3- to 12-membered heterocyclic group containing at least one ring heteroatom selected from the group consisting of nitrogen, oxygen and sulfur, optionally substituted by $COOR^{6b}$;

$R^{6a}$, $R^{6b}$, $R^7$, $R^8$ and $R^9$ are selected from H, $C_1$-$C_8$-alkyl and $C_7$-$C_{14}$-aralkyl; and $R^{10}$ is $C_1$-$C_8$-alkyl optionally substituted by halogen, $C_6$-$C_{10}$-aryl optionally substituted by OH, $C_1$-$C_8$-alkyl, O—$C_1$-$C_8$-alkyl or -halogen, or $NR^{4a}R^{4b}$;

A is selected from -E-$NR^{14}$—, -E-$NR^{14}$-G-$NR^{15}$—, -E-$NR^{14}$C(O)$NR^{14}$-G-$NR^{15}$—, -E-$NR^{14}$C(O)G-

$NR^{15}$—, -E-$NR^{14}$-G-$NR^{14}$-$E^a$, —$NR^{14}$C(O)-E-$NR^{14}$C(O)$NR^{14}$—, —$NR^{15}$-G-$NR^5$—, —$NR^{15}$—(C$R^{16}$$R^{17}$)$_n$—$NR^{15}$—, —$NR^{15}$-X3-G-X4-$NR^{15}$, —$NR^{14}$C(O)$NR^{14}$—, $NR^{14}$C(O)$NR^{14}$-J-$NR^{15}$—, $NR^{14}$C(O)—(C$R^{16}$$R^{17}$), —C(O)$NR^{14}$—, and $NR^{14}$C(O)$NR^{14}$-E-$NR^{14}$C(O)$NR14^4$-;

E is selected from $C_3$-$C_{15}$-carbocyclic group optionally substituted by HO, $C_1$-$C_8$-alkyl, $C_6$-$C_{10}$-aryl, 3- to 12-membered heterocyclic group, a $C_6$-$C_{10}$-aryl optionally substituted by HO, $C_1$-$C_8$-alkyl, O—$C_1$-$C_8$-alkyl, halogen, and -$E^a$-C(O)$NR^{14}$-$E^b$-$NR^{14}$C(O)-$E^a$;

each $E^a$ is independently selected from a 3- to 12-membered heterocyclic group containing from 1-4 ring nitrogen atoms and optionally containing from 1-4 other heteroatoms selected from the group consisting of oxygen and sulfur, a $C_3$-$C_{15}$-carbocyclic group, and $C_6$-$C_{10}$-aryl optionally substituted by HO, $C_1$-$C_8$-alkyl, O—$C_1$-$C_8$-alkyl, or halogen;

$E^b$ is selected from a 3- to 12-membered heterocyclic group containing from 1-4 ring nitrogen atoms and optionally containing from 1-4 other heteroatoms selected from the group consisting of oxygen and sulfur, a $C_3$-$C_{15}$-carbocyclic group, and $C_6$-$C_{10}$-aryl optionally substituted by HO, $C_1$-$C_8$-alkyl, O—$C_1$-$C_8$-alkyl, or halogen;

G is selected from selected from C(O), $NR^{14}$C(O), C(O)$NR^{14}$, $C_1$-$C_8$-alkyl optionally substituted by OH, halogen or $C_6$-$C_{10}$-aryl, a 3- to 12-membered heterocyclic group containing from 1-4 ring nitrogen atoms and optionally containing from 1-4 other heteroatoms selected from the group consisting of oxygen and sulfur optionally substituted by $R^{18}$, a $C_3$-$C_{15}$-carbocyclic group optionally substituted by HO, $C_1$-$C_8$-alkyl, and $C_6$-$C_{10}$-aryl optionally substituted by HO, $C_1$-$C_8$-alkyl, O—$C_1$-$C_8$-alkyl, or halogen;

J is selected from $C_6$-$C_{10}$-aryl, $SO_2$, and $C_6$-$C_{10}$-aryl-$SO_2$—;

X3 and X4 are independently selected from $C_1$-$C_8$-alkyl optionally substituted by OH, halogen or $C_6$-$C_{10}$-aryl, a 3- to 12-membered heterocyclic group containing from 1-4 ring nitrogen atoms and optionally containing from 1-4 other heteroatoms consisting of oxygen and sulfur optionally substituted by $R^{18}$, a $C_3$-$C_{15}$-carbocyclic group, and $C_6$-$C_{10}$-aryl;

each $R^{14}$ is independently selected from H, $C_1$-$C_8$-alkyl, and $C_6$-$C_{10}$-aryl;

each $R^{15}$ is independently selected from H, —CN, $C_1$-$C_8$-alkyl, and $C_6$-$C_{10}$-aryl;

each $R^{16}$ and each $R^{17}$ are independently selected from H, halogen, OH, $C_1$-$C_8$-alkyl, and $C_6$-$C_{10}$-aryl;

$R^{18}$ is 3- or 12-membered heterocyclic ring containing at least one ring heteroatom selected from the group consisting of nitrogen, oxygen and sulfur, said 3- or 12-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl or O—$C_1$-$C_8$-alkyl optionally substituted by aminocarbonyl; and n is an integer selected from 1-8.

DEFINITIONS

Terms used in the specification have the following meanings:

"Optionally substituted" means the group referred to can be substituted at one or more positions by any one or any combination of the radicals listed thereafter.

"Halo" or "halogen", as used herein, may be fluorine, chlorine, bromine or iodine. Preferably halo is chlorine.

"Hydroxy", as used herein, is OH.

"$C_1$-$C_8$-Alkyl", as used herein, denotes straight chain or branched alkyl having 1-8 carbon atoms. Preferably $C_1$-$C_8$-alkyl is $C_1$-$C_4$-alkyl.

"$C_1$-$C_8$-Alkoxy", or as used herein, denotes straight chain or branched alkoxy having 1-8 carbon atoms (e.g., O—$C_1$-$C_8$-alkyl). Preferably, $C_1$-$C_8$-alkoxy is $C_1$-$C_4$-alkoxy.

"$C_3$-$C_8$-Cycloalkyl", as used herein, denotes cycloalkyl having 3-8 ring carbon atoms, e.g., a monocyclic group, such as a cyclopropyl, cyclobutyl, cyclopentyl, cyclohexyl, cycloheptyl or cyclooctyl, any of which can be substituted by one or more, usually one or two, $C_1$-$C_4$-alkyl groups; or a bicyclic group, such as bicycloheptyl or bicyclooctyl.

"$C_1$-$C_8$-Alkylamino" and "di($C_1$-$C_8$-alkyl)amino", as used herein, denote amino substituted respectively by one or two $C_1$-$C_8$-alkyl groups as hereinbefore defined, which may be the same or different.

"$C_1$-$C_8$-Alkylcarbonyl" and "$C_1$-$C_8$-alkoxycarbonyl", as used herein, denote $C_1$-$C_8$-alkyl or $C_1$-$C_8$-alkoxy, respectively, as hereinbefore defined attached by a carbon atom to a carbonyl group.

"$C_6$-$C_{10}$-Aryl", as used herein, denotes a monovalent carbocyclic aromatic group that contains 6-10 carbon atoms and which may be, e.g., a monocyclic group, such as phenyl; or a bicyclic group, such as naphthyl.

"$C_7$-$C_{14}$-Aralkyl", as used herein, denotes alkyl, e.g., $C_1$-$C_4$-alkyl, as hereinbefore defined, substituted by $C_6$-$C_{10}$-aryl as hereinbefore defined. Preferably, $C_7$-$C_{14}$-aralkyl is $C_7$-$C_{10}$-aralkyl, such as phenyl-$C_1$-$C_4$-alkyl.

"$C_1$-$C_8$-Alkylaminocarbonyl" and "$C_3$-$C_8$-cycloalkylaminocarbonyl", as used herein, denote $C_1$-$C_8$-alkylamino and $C_3$-$C_8$-cycloalkylamino respectively as hereinbefore defined attached by a carbon atom to a carbonyl group. Preferably $C_1$-$C_8$-alkylaminocarbonyl and $C_3$-$C_8$-cycloalkyl-aminocarbonyl are $C_1$-$C_4$-alkylaminocarbonyl and $C_3$-$C_8$-cycloalkylaminocarbonyl, respectively.

"$C_3$-$C_{15}$-Carbocyclic group", as used herein, denotes a carbocyclic group having 3-15 ring carbon atoms, e.g., a monocyclic group, either aromatic or non-aromatic, such as a cyclopentyl, cyclohexyl, cycloheptyl, cyclooctyl or phenyl; or a bicyclic group, such as bicyclooctyl, bicyclononyl, bicyclodecyl, indanyl or indenyl, again any of which can be substituted by one or more, usually one or two, $C_1$-$C_4$-alkyl groups. Preferably the $C_3$-$C_{15}$-carbocyclic group is a $C_5$-$C_{10}$-carbocyclic group, especially phenyl, cyclohexyl or indanyl. The $C_5$-$C_{15}$-carbocyclic group can unsubstituted or substituted. Substituents on the heterocyclic ring include halo, cyano, OH, carboxy, amino, aminocarbonyl, nitro, $C_1$-$C_{10}$-alkyl, $C_1$-$C_{10}$-alkoxy and $C_3$-$C_{10}$-cycloalkyl.

"3- to 12-Membered heterocyclic ring containing at least one ring heteroatom selected from the group consisting of nitrogen, oxygen and sulfur", as used herein, may be, e.g., furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, morpholino, triazine, oxazine or thiazole. Preferred heterocyclic rings include piperazine, pyrrolidine, morpholino, imidazole, isotriazole, pyrazole, tetrazole, thiazole, triazole, thiadiazole, pyridine, piperidine, pyrazine, furan, oxazole, isoxazole, oxadiazole and azetidine. The 3-to-12-membered heterocyclic ring can be unsubstituted or substituted.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps. As understood by one skilled in the art only combinations of substituents that are chemically possible are embodiments of the invention.

Especially preferred specific compounds of formula (I) are those described hereinafter in the Examples.

Stereoisomers are those compounds where there is an asymmetric carbon atom. The compounds exist in individual optically active isomeric forms or as mixtures thereof, e.g., as diastereomeric mixtures. The present invention embraces both individual optically active R and S isomers, as well as mixtures thereof. Individual isomers can be separated by methods well known to those skilled in the art, e.g., chiral high performance liquid chromatography (HPLC).

Tautomers are one of two or more structural isomers that exist in equilibrium and are readily converted from one isomeric form to another.

The compounds of the invention may exist in both unsolvated and solvated forms. The term "solvate" is used herein to describe a molecular complex comprising the compound of the invention and one or more pharmaceutically acceptable solvent molecules, for example, ethanol. The term "hydrate" is employed when said solvent is water.

According to formula (I), $R^{1a}$ and $R^{1b}$ are, independently, suitably a N-bonded 3- to 12-membered heterocyclic group containing from 1-4 ring nitrogen atoms and optionally containing from 1-4 other heteroatoms selected from the group consisting of oxygen and sulfur, that group being optionally substituted by oxo, O—$C_1$-$C_8$-alkyl, $C_6$-$C_{10}$-aryl, $R^{1c}$ or by $C_1$-$C_8$-alkyl optionally substituted by OH. The 3- to 12-membered heterocyclic groups are preferably 5- to 6-membered heterocyclic groups (e.g., tetrazole groups, pyrrole groups, pyrazole groups, pyridine groups, isoxazole groups, triazole groups, or hydantoin groups). The $R^{1a}$ and $R^{1b}$ heterocyclic groups can be N-bonded where possible. The heterocyclic groups are preferably substituted by at least one group selected from $C_1$-$C_8$-alkyl optionally substituted by OH (e.g., an ethyl group, a hydroxymethyl group or a hydroxyethyl group). These substitution groups on the heterocyclic groups can be C- or N-bonded to the heterocyclic group where possible.

According to formula (I), $R^{1a}$ and $R^{1b}$ are also, independently, suitably —NH—$C_1$-$C_8$-alkylcarbonyl or —NH—$C_3$-$C_8$-cycloalkylcarbonyl. The —NH—$C_1$-$C_8$-alkylcarbonyl group is preferably a acetamide group or a propionamide group. The —NH—$C_3$-$C_8$-cycloalkylcarbonyl is preferably a cyclobutane carboxylic acid amide group.

According to formula (I), $R^{1a}$ and $R^{1b}$ are also, independently suitably $C_1$-$C_8$-hydroxy alkyl or $CH_2$—O—$C_1$-$C_8$-alkyl.

According to formula (I) $R^{1a}$ and $R^{1b}$ are also, independently, suitably NHC(O)$C_1$-$C_8$-hydroxyalkyl. $R^1$ is preferably NHC(O)$C_1$-$C_2$ hydroxyalkyl (e.g., a 2-hydroxy-acetamide group, a 2-hydroxy-propionamide group, or a 3-hydroxy-propionamide group).

According to formula (I), $R^2$ is suitably H, $C_1$-$C_8$-alkyl optionally substituted by OH, halogen or $C_6$-$C_{10}$-aryl optionally substituted by OH or O—$C_1$-$C_8$ alkyl. When substituted, suitably the $C_1$-$C_8$-alkyl is substituted by OH, phenyl, napthalene, or preferably by two phenyl groups. When the $C_1$-$C_8$-alkyl is substituted by two phenyl groups, either or both phenyl groups are preferably unsubstituted, or substituted by at least one $OCH_3$, one OH or one halogen.

According to formula (I), $R^2$ is also suitably $C_1$-$C_8$-alkyl substituted by a phenyl. This phenyl can be further substituted by a phenyl where this phenyl is substituted by CN, halogen, or $C_1$-$C_8$-alkyl.

According to formula (I), $R^2$ is also suitably a $C_3$-$C_{15}$-carbocyclic group (e.g., a fluorene group).

According to formula (I), $R^3$ is suitably selected from amino substituted by $R^{3c}$, —$R^{3c}$— $C_7$-$C_{14}$-aralkyl, $C_1$-$C_8$-alkyl optionally substituted by $R^{3c}$, and a $C_3$-$C_{15}$-carbocyclic group optionally substituted by OH, $C_1$-$C_8$-alkyl or $C_1$-$C_8$-alkoxycarbonyl. $R^{3c}$ is suitably a 3- to 12-membered heterocyclic group containing at least one ring heteroatom selected from the group consisting of nitrogen, oxygen and sulfur (e.g., a pyrrolidine or a pyrazole) optionally substituted by halo, cyano, oxo, OH, carboxy, nitro, $C_1$-$C_8$-alkyl, $C_1$-$C_8$-alkylcarbonyl, OH—$C_1$-$C_8$-alkyl, $C_1$-$C_8$-haloalkyl, amino-$C_1$-$C_8$-alkyl, amino(OH)$C_1$-$C_8$-alkyl and $C_1$-$C_8$-alkoxy optionally substituted by aminocarbonyl. Preferably the 3- to 12-membered heterocyclic group is substituted by at least one $C_1$-$C_8$-alkyl group.

According to formula (I), $R^3$ is also independently suitably a N-bonded 3- to 12-membered heterocyclic group containing at least one ring heteroatom selected from the group consisting of nitrogen, oxygen and sulfur. This heterocyclic group is preferably a pyrrolidine, pyrazole, triazole, tetrazole or imidazole. The heterocyclic group is optionally substituted by $NR^{4f}C(O)NR^{4g}R^{4h}$, $NR^{4a}R^{4b}$, $NHC(O)R^{20q}$ and where $R^{4a}$ and $R^{4b}$ are preferably H or $C_1$-$C_8$-alkyl (e.g., methyl) and $R^{4f}$ and $R^{4h}$ are preferably H. $R^{4g}$ is preferably a 3- to 12-membered heterocyclic group, such as pyridine.

According to formula (I), $R^3$ is also suitably $C_6$-$C_{10}$-aryl optionally substituted by OH, $C_1$-$C_8$-alkyl, O—$C_1$-$C_8$-alkyl, $SO_2R^{10}$ or -halogen, where $R^{10}$ is suitably $NH_2$.

According to formula (I), A is suitably selected from -E-$NR^{14}$—, -E-$NR^{14}$-G-$NR^{14}$—, -E-$NR^{14}$C(O)$NR^{14}$-G-$NR^{14}$, -E-$NR^{14}$C(O)G-$NR^{15}$—, -E-$NR^{14}$-G-$NR^{14}$-$E^a$-, E is suitably selected from 5-6 heterocyclic group, such as pyrrolidine and piperidine. Ea is suitably $C_3$-$C_{15}$-carbocyclic group, such as cyclohexyl. Each $R^{14}$ is independently suitably selected from H and $C_1$-$C_8$-alkyl, such as methyl. G is suitably selected a $C_3$-$C_{15}$-carbocyclic group optionally substituted by HO or $C_1$-$C_8$-alkyl or G is suitably selected from 5-6 heterocyclic group, such as pyrrolidine and piperidine. Preferably the $C_3$-$C_{15}$-carbocyclic group is unsubstituted.

Another aspect of the invention provides compounds of formula (Ia), or stereoisomers or pharmaceutically acceptable salts thereof,

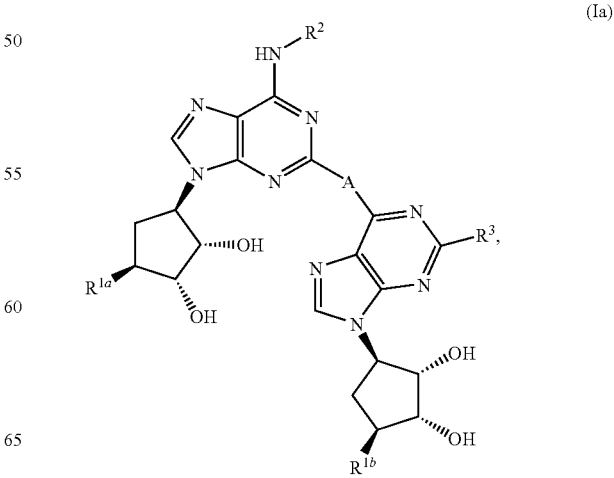

(Ia)

wherein $R^1$ and $R^{1b}$ are independently selected from a 3- to 12-membered heterocyclic group containing from 1-4 ring nitrogen atoms and optionally containing from 1-4 other heteroatoms selected from the group consisting of oxygen and sulfur, that group being optionally substituted by oxo, O—$C_1$-$C_8$-alkyl, $C_6$-$C_{10}$-aryl, $R^{1c}$ or by $C_1$-$C_8$-alkyl optionally substituted by OH, or $R^1$ and $R^{1b}$ are independently selected from —$NR^4R^4$, and —$NR^5$—$C_1$-$C_8$-alkylcarbonyl;

$R^2$ is $C_1$-$C_8$-alkyl optionally substituted by OH, halogen $C_6$-$C_{10}$-aryl optionally substituted by OH, $SC_1$-$C_8$-alkyl, CN, halogen, O—$C_7$-$C_{14}$-aralkyl, or O—$C_1$-$C_8$-alkyl, a $C_3$-$C_{15}$-carbocyclic group optionally substituted by O—$C_7$-$C_{14}$ aralkyl, $C_3$-$C_{15}$-carbocyclic group, O—$C_1$-$C_8$-alkyl, $C_2$-$C_8$-alkenyl, $C_2$-$C_8$-alkynyl or $C_1$-$C_8$-alkyl, O—$C_1$-$C_8$-alkyl, —$SO_2$—$C_1$-$C_8$-alkyl, a 3- to 12-membered heterocyclic group containing from 1-4 ring nitrogen atoms and optionally containing from 1-4 other heteroatoms selected from the group consisting of oxygen and sulfur, that group being optionally substituted by 3- to 12-membered heterocyclic group containing from 1-4 ring nitrogen atoms and optionally containing from 1-4 other heteroatoms selected from the group consisting of oxygen and sulfur, $C_7$-$C_{14}$-aralkyl, or $C_6$-$C_{14}$-aryl optionally substituted by O—$C_7$-$C_{14}$-aralkyl, or $R^3$ is hydrogen, halo, $C_2$-$C_8$-alkenyl, $C_2$-$C_8$-alkynyl or $C_1$-$C_8$-alkoxycarbonyl, or $R^3$ is $C_1$-$C_8$-alkylamino optionally substituted by OH, $R^{3b}$, amino, di($C_1$-$C_8$-alkyl)amino, —NH—C(=O)—$C_1$-$C_8$-alkyl, —NH—$SO_2$—$C_1$-$C_8$-alkyl, —NH—C(=O)—NH—$R^{3c}$, —NH—C(=O)—NH—$C_1$-$C_8$-alkyl-$R^{3b}$, a $C_3$-$C_{15}$-carbocyclic group or by $C_6$-$C_{10}$-aryl optionally substituted by $C_6$-$C_{10}$-aryloxy, or $R^3$ is a 3- to 12-membered heterocyclic group containing from 1-4 ring nitrogen atoms and optionally containing from 1-4 other heteroatoms selected from the group consisting of oxygen and sulfur, that group being optionally substituted by 0-3$R^4$;

$R^{3a}$ and $R^{3b}$ are each independently a 3- to 12-membered heterocyclic group containing at least one ring heteroatom selected from the group consisting of nitrogen, oxygen and sulfur; optionally substituted by halo, cyano, oxo, OH, carboxy, nitro, $C_1$-$C_8$-alkyl, $C_1$-$C_8$-alkylcarbonyl, OH—$C_1$-$C_8$-alkyl, $C_1$-$C_8$-haloalkyl, amino-$C_1$-$C_8$-alkyl, amino(OH)$C_1$-$C_8$-alkyl and $C_1$-$C_8$-alkoxy optionally substituted by aminocarbonyl;

$R^{3c}$ is a 5- or 6-membered heterocyclic group containing at least one ring heteroatom selected from the group consisting of nitrogen, oxygen and sulfur, which is optionally substituted by a 5- or 6-membered heterocyclic group containing at least one ring heteroatom selected from the group consisting of nitrogen, oxygen and sulfur;

$R^{3d}$ are independently a 5- or 6-membered heterocyclic ring containing at least one ring heteroatom selected from the group consisting of nitrogen, oxygen and sulfur, said 5- or 6-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl, $C_1$-$C_8$-alkoxy optionally substituted by aminocarbonyl, or a 5- or 6-membered heterocyclic ring containing at least one ring heteroatom selected from the group consisting of nitrogen, oxygen and sulfur, said ring also being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl, or $C_1$-$C_8$-alkoxy optionally substituted by aminocarbonyl;

$R^4$ is selected from OH, $C_1$-$C_8$-alkyl optionally substituted by OH, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl or -halogen, O—$C_6$-$C_{10}$-aryl optionally substituted by OH, $C_1$-$C_8$-alkyl, O—$C_1$-$C_8$-alkyl or -halogen, $NR^{4f}C(O)NR^{4g}R^{4h}$;

$R^{4f}$, $R^{4h}$ are, independently, H, or $C_1$-$C_8$-alkyl;

$R^{4g}$ is a 3- to 12-membered heterocyclic group containing at least one ring heteroatom selected from the group consisting of nitrogen, oxygen and sulphur;

A is selected from -E-$NR^{14}$—, -E-$NR^{14}$-G-$NR^{15}$—, -E-$NR^{14}C(O)NR^{14}$-G-$NR^{15}$—, -E-$NR^{14}C(O)G$-$NR^{15}$—, -E-$NR^{14}$-G-$NR^{14}$-E- and —$NR^{15}$-G-$NR^{15}$—;

E is selected from $C_3$-$C_{15}$-carbocyclic group optionally substituted by HO, $C_1$-$C_8$-alkyl, $C_6$-$C_{10}$-aryl, 3- to 12-membered heterocyclic group, a $C_6$-$C_{10}$-aryl optionally substituted by HO, $C_1$-$C_8$-alkyl, O—$C_1$-$C_8$-alkyl, halogen, or -$E^a$-C(O)$NR^{14}$-$E^b$-$NR^{14}C(O)$-$E^a$-;

each $E^a$ is independently selected from a 3- to 12-membered heterocyclic group containing from 1-4 ring nitrogen atoms and optionally containing from 1-4 other heteroatoms selected from the group consisting of oxygen and sulfur, a $C_3$-$C_{15}$-carbocyclic group, and $C_6$-$C_{10}$-aryl optionally substituted by HO, $C_1$-$C_8$-alkyl, O—$C_1$-$C_8$-alkyl, or halogen;

$E^b$ is selected from a 3- to 12-membered heterocyclic group containing from 1-4 ring nitrogen atoms and optionally containing from 1-4 other heteroatoms selected from the group consisting of oxygen and sulfur, a $C_3$-$C_{15}$-carbocyclic group, and $C_6$-$C_{10}$-aryl optionally substituted by HO, $C_1$-$C_8$-alkyl, O—$C_1$-$C_8$-alkyl, or halogen;

G is selected from selected from C(O), $NR^{14}C(O)$, C(O)$NR^{14}$, $C_1$-$C_8$-alkyl optionally substituted by OH, halogen or $C_6$-$C_{10}$-aryl, a 3- to 12-membered heterocyclic group containing from 1-4 ring nitrogen atoms and optionally containing from 1-4 other heteroatoms selected from the group consisting of oxygen and sulfur optionally substituted by $R^{18}$, a $C_3$-$C_{15}$-carbocyclic group optionally substituted by HO, $C_1$-$C_8$-alkyl, and $C_6$-$C_{10}$-aryl optionally substituted by HO, $C_1$-$C_8$-alkyl, or O—$C_1$-$C_8$-alkyl, halogen; and $R^{18}$ is 3- or 12-membered heterocyclic ring containing at least one ring heteroatom selected from the group consisting of nitrogen, oxygen and sulfur, said 3- or 12-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl or O—$C_1$-$C_8$-alkyl optionally substituted by aminocarbonyl.

Another aspect of the invention provides compounds of formula (Ia), or stereoisomers or pharmaceutically acceptable salts thereof, wherein $R^1$ and $R^{1b}$ are independently selected from a 3- to 12-membered heterocyclic group containing from 1-4 ring nitrogen atoms and optionally containing from 1-4 other heteroatoms selected from the group consisting of oxygen and sulfur, that group being optionally substituted by oxo, O—$C_1$-$C_8$-alkyl, $C_6$-$C_{10}$-aryl, $R^{1c}$ or by $C_1$-$C_6$-alkyl optionally substituted by OH, or $R^1$ and $R^{1b}$ are independently selected from —$NR^4R^4$, and —$NR^5$—$C_1$-$C_8$-alkylcarbonyl;

R² is C₁-C₈-alkyl optionally substituted by OH, halogen C₆-C₁₀-aryl optionally substituted by OH, SC₁-C₈-alkyl, CN, halogen, O—C₇-C₁₄-aralkyl, or O—C₁-C₈-alkyl, a C₃-C₁₅-carbocyclic group optionally substituted by O—C₇-C₁₄ aralkyl, C₃-C₁₅-carbocyclic group, O—C₁-C₈-alkyl, C₂-C₈-alkenyl, C₂-C₈-alkynyl or C₁-C₈-alkyl, O—C₁-C₈-alkyl, —SO₂—C₁-C₈-alkyl, a 3- to 12-membered heterocyclic group containing from 1-4 ring nitrogen atoms and optionally containing from 1-4 other heteroatoms selected from the group consisting of oxygen and sulfur, that group being optionally substituted by 3- to 12-membered heterocyclic group containing from 1-4 ring nitrogen atoms and optionally containing from 1-4 other heteroatoms selected from the group consisting of oxygen and sulfur, C₇-C₁₄-aralkyl, or C₆-C₁₄-aryl optionally substituted by O—C₇-C₁₄-aralkyl, or R³ is hydrogen, halo, C₂-C₈-alkenyl, C₂-C₈-alkynyl or C₁-C₈-alkoxycarbonyl, or R³ is C₁-C₈-alkylamino optionally substituted by OH, R³ᵇ, amino, di(C₁-C₈-alkyl)amino, —NH—C(=O)—C₁-C₈-alkyl, —NH—SO₂—C₁-C₈-alkyl, —NH—C(=O)—NH—R³ᶜ, —NH—C(=O)—NH—C₁-C₈-alkyl-R³ᵇ, a C₃-C₁₅-carbocyclic group or by C₆-C₁₀-aryl optionally substituted by C₆-C₁₀-aryloxy, or R³ is a 3- to 12-membered heterocyclic group containing from 1-4 ring nitrogen atoms and optionally containing from 1-4 other heteroatoms selected from the group consisting of oxygen and sulfur, that group being optionally substituted by 0-3R⁴;

R³ᵃ and R³ᵇ are each independently a 3- to 12-membered heterocyclic group containing at least one ring heteroatom selected from the group consisting of nitrogen, oxygen and sulfur; optionally substituted by halo, cyano, oxo, OH, carboxy, nitro, C₁-C₈-alkyl, C₁-C₈-alkylcarbonyl, OH—C₁-C₈-alkyl, C₁-C₈-haloalkyl, amino-C₁-C₈-alkyl, amino(OH)C₁-C₈-alkyl or C₁-C₈-alkoxy optionally substituted by aminocarbonyl;

R³ᶜ is a 5- or 6-membered heterocyclic group containing at least one ring heteroatom selected from the group consisting of nitrogen, oxygen and sulfur, which is optionally substituted by a 5- or 6-membered heterocyclic group containing at least one ring heteroatom selected from the group consisting of nitrogen, oxygen and sulfur;

R³ᵈ are independently a 5- or 6-membered heterocyclic ring containing at least one ring heteroatom selected from the group consisting of nitrogen, oxygen and sulfur, said 5- or 6-membered heterocyclic ring being optionally substituted by halo, cyano, oxo, OH, carboxy, amino, nitro, C₁-C₈-alkyl, C₁-C₈-alkylsulfonyl, aminocarbonyl, C₁-C₈-alkylcarbonyl, C₁-C₈-alkoxy optionally substituted by aminocarbonyl, or a 5- or 6-membered heterocyclic ring containing at least one ring heteroatom selected from the group consisting of nitrogen, oxygen and sulfur, said ring also being optionally substituted by halo, cyano, oxo, OH, carboxy, amino, nitro, C₁-C₈-alkyl, C₁-C₈-alkylsulfonyl, aminocarbonyl, C₁-C₈-alkylcarbonyl, C₁-C₈-alkoxy optionally substituted by aminocarbonyl;

R⁴ is selected from OH, C₁-C₈-alkyl optionally substituted by OH, C₁-C₈-alkoxy, C₇-C₁₄-aralkyl optionally substituted with OH, O—C₁-C₈-alkyl, halogen C₆-C₁₀-aryl, or O—C₆-C₁₀-aryl, C₁-C₈-alkoxy, C₆-C₁₀-aryl optionally substituted by OH, C₁-C₈-alkyl, O—C₁-C₈-alkyl or -halogen, O—C₆-C₁₀-aryl optionally substituted by OH, C₁-C₈-alkyl, O—C₁-C₈-alkyl or -halogen, and NR⁴ᶠC(O)NR⁴ᵍR⁴ʰ;

R⁴ᶠ, R⁴ʰ are, independently, H, or C₁-C₈-alkyl;

R⁴ᵍ is a 3- to 12-membered heterocyclic group containing at least one ring heteroatom selected from the group consisting of nitrogen, oxygen and sulphur; and A is selected from

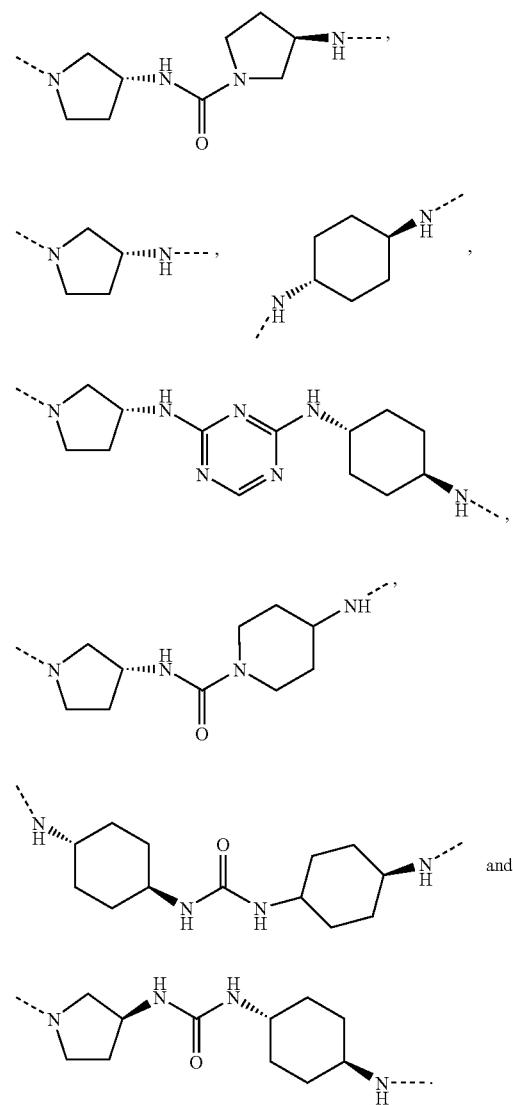

Synthesis

Another embodiment of the present invention provides a process for the preparation of compounds of formula (I), in free or pharmaceutically acceptable salt form, which comprises the steps of:

(i) reacting a compound of formula (II)

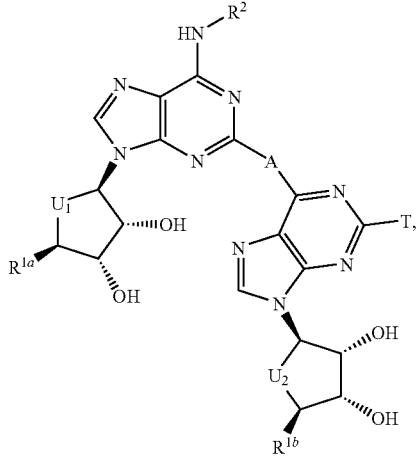
(II)

where
$R^{1a}$, $R^{1b}$, $R^2$, $U_1$, $U_2$ are as defined hereinbefore; and
T is a leaving group with a compound of formula (III)

H—$R^3$ (III), where $R^3$ is as defined hereinbefore; and (ii) removing any protecting groups and recovering the resultant compound of formula (II), in free or pharmaceutically acceptable salt form.

The compound of formula (II) may be prepared by reacting a compound of formula (IV)

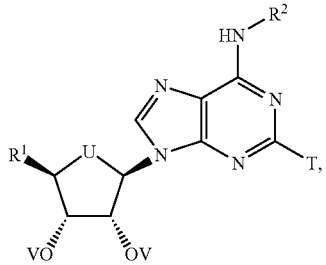
(IV)

wherein
$R^1$ is equivalent to $R^{1a}$ and $R^{1b}$.
$R^2$ and U is equivalent to $U_1$ and $U_2$, and are as defined in claim 1;
V is H or a protecting group;
T is a leaving group, with a compound of formula H-A-V, where A is as defined hereinbefore; and
V is H or a protecting group to provide a compound of formula (VI)

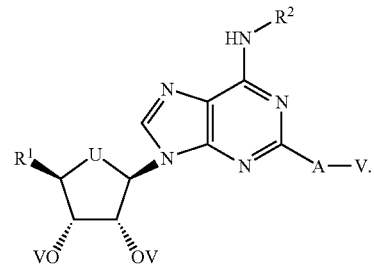
(VI)

Compound (VI) can be reacted with a compound of formula (VII)

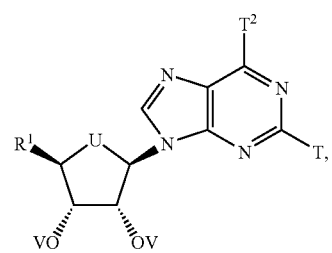
(VII)

wherein
$R^1$ is equivalent to $R^{1a}$ and $R^{1b}$;
U is equivalent to $U_1$ and $U_2$;
V are defined in claim 1; and
T and $T^2$ are halogen.

The compound of formula (VII) may be prepared by reacting a compound of formula (VIII)

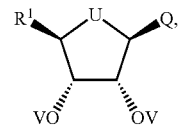
(VIII)

wherein
$R^1$ is equivalent to $R^{1a}$ and $R^{1b}$;
U is equivalent to $U_1$ and $U_2$;
V are as defined in claim 1; and
Q represents a leaving group or a protected derivative thereof with a 2,6-dihalopurine, e.g., 2,6-dichloropurine to provide a compound of formula (VII)

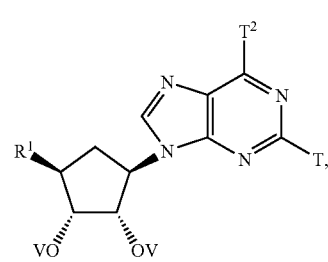
(VIII)

wherein
$R^1$ is equivalent to $R^{1a}$ and $R^{1b}$;

U is equivalent to $U_1$ and $U_2$;
V are defined in claim 1; and
T and $T^2$ are halogen.

The compounds of formula (I) can be prepared, for example, using the reactions and techniques described below and in the Examples. The compounds of formula (I) can be prepared analogously to the preparations described in Applicant's patent applications WO/2006/045552 and WO 2006/074925. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I) Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5$^{th}$ Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups In Organic Synthesis*, Wiley and Sons (1999). It is understood by those skilled in the art that only combinations of substituents that are chemically possible are embodiments of the present invention.

Compounds of formula (I) in free form may be converted into salt form, and vice versa, in a conventional manner. The compounds in free or salt form can be obtained in the form of hydrates or solvates containing a solvent used for crystallization. Compounds of formula (I) can be recovered from reaction mixtures and purified in a conventional manner. Isomers, such as stereoisomers, may be obtained in a conventional manner, e.g., by fractional crystallization or asymmetric synthesis from correspondingly asymmetrically substituted, e.g., optically active, starting materials.

Compounds of formula (I) and their pharmaceutically acceptable salts are useful as pharmaceuticals. In particular, they activate the adenosine $A_{2A}$ receptor, i.e., they act as $A_{2A}$ receptor agonists. Their properties as $A_{2A}$ agonists may be demonstrated using the method described by Murphree et al., *Mol Pharmacol*, Vol. 61, pp. 455-462 (2002).

Compounds of the Examples hereinbelow have $K_i$ values below 1.0 μM in the above assay. For example, the compound of Example 1 has a $K_i$ value of 0.76 μM.

Having regard to their activation of the adenosine $A_{2A}$ receptor, compounds of formula (I), in free or pharmaceutically acceptable salt form, hereinafter alternately referred to as "agents of the invention", are useful in the treatment of conditions which respond to the activation of the adenosine $A_{2A}$ receptor, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Other inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, for example, anti-inflammatory (e.g., cortico-steroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g., between the hours of about 4-6 am, i.e., at a time normally substantially distant from any previously administered symptomatic asthma therapy.

Having regard to their anti-inflammatory activity, in particular in relation to inhibition of eosinophil activation, agents of the invention are also useful in the treatment of eosinophil related disorders, e.g., eosinophilia, in particular eosinophil related disorders of the airways (e.g., involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular, metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular, diseases or conditions having an inflammatory component, for example, treatment of diseases and conditions of the eye, such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g., hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g., ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g., including idiopathic nephrotic syndrome or minimal change nephropathy).

Further, agents of the invention may also be used for the treatment of cystic fibrosis, pulmonary hypertension, pulmonary fibrosis, inflammatory bowel syndrome, wound healing, diabetic nephropathy as described in WO 05/107463, reduction of inflammation in transplanted tissue as described in US 2005/182018, inflammatory diseases caused by pathogenic organisms as described in WO 03/086408, and cardiovascular conditions as described in WO 03/029264.

Also, the agents of the invention may be used to assess the severity of coronary artery stenosis as described in WO 00/078774 and useful in conjunction with radioactive imaging agents to image coronary activity and useful in adjunctive therapy with angioplasty as described in WO 00/78779.

Agents of the invention are also useful in combination with a protease inhibitor for prevention of organ ischemia and reperfusion injury as described in WO 05/003150, and in combination with an integrin antagonist for treating platelet aggregation as described in WO 03/090733.

Agents of the invention are also useful in promoting wound healing in bronchial epithelial cells as described in AJP-Lung, Vol. 290, pp. 849-855.

Other diseases or conditions which may be treated with agents of the invention include diabetes, e.g., diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, conditions characterized by elevated intraocular pressure or secretion of ocular aqueous humor, such as glaucoma, ischemic tissue/organ damage from reperfusion and bedsores.

The effectiveness of an agent of the invention in inhibiting inflammatory conditions, for example, in inflammatory airways diseases, may be demonstrated in an animal model, e.g., a mouse or rat model, of airways inflammation or other inflammatory conditions, for example, as described by Szarka et al, J Immunol Methods, Vol. 202, pp. 49-57 (1997); Renzi et al., Am Rev Respir Dis, Vol. 148, pp. 932-939 (1993); Tsuyuki et al., J Clin Invest Vol. 86, pp. 2924-2931 (1995); Cernadas et al., Am J Respir Cell Mol Biol, Vol. 20, pp. 1-8 (1999); and Fozard et al., Eur J Pharmacol, Vol. 438, pp. 183-188 (2002).

The agents of the invention are also useful as co-therapeutic agents for use in combination with other drug substances, such as anti-inflammatory, bronchodilatory, antihistamine or anti-tussive drug substances, particularly in the treatment of obstructive or inflammatory airways diseases such as those mentioned hereinbefore, for example, as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance.

Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Suitable anti-inflammatory drugs include steroids, in particular, glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTB4 antagonists, such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700; LTD4 antagonists such include montelukast, pranlukast, zafirlukast, accolate, SR2640, Wy-48,252, ICI 198615, MK-571, LY-171883, Ro 245913 and L-648051; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine AB receptor antagonists, such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 00/75114, which document is incorporated herein by reference, preferably compounds of the Examples thereof, especially a compound of formula

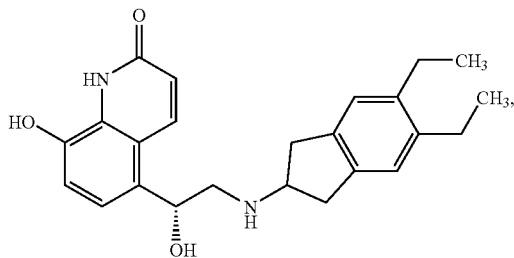

and pharmaceutically acceptable salts thereof, as well as compounds (in free or salt or solvate form) of formula (I) of WO 04/16601, and also compounds of EP 1440966, JP 05025045, WO 93/18007, WO 99/64035, US 2002/0055651, US 2005/0133417, US 2005/5159448, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, EP 1460064, WO 04/087142, WO 04/089892, EP 01477167, US 2004/0242622, US 2004/0229904, WO 04/108675, WO 04/108676, WO 05/033121, WO 05/040103, WO 05/044787, WO 05/058867, WO 05/065650, WO 05/066140, WO 05/07908, WO 2007018461, WO 2007027133, WO 2006051373, WO 2006056471, and WO 2004016601.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/018422, WO 04/05285 and WO 05/077361.

Suitable dual antiinflammatory and bronchodilatory drugs include dual beta-2 adrenoceptor agonist/muscarinic antagonists such as those disclosed in US 2004/0167167, US 2004/0242622, US 2005/182092, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

Other useful combinations of agents of the invention with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D, Takeda antagonists, such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

In accordance with the foregoing, the invention also provides a method for the treatment of a condition responsive to activation of the adenosine $A_{2A}$ receptor, for example, an inflammatory or allergic condition, particularly an inflammatory or obstructive airways disease, which comprises administering to a subject, particularly a human subject, in need thereof a compound of formula (I) in free form or in the form of a pharmaceutically acceptable salt. In another aspect the invention provides a compound of formula (I), in free form or in the form of a pharmaceutically acceptable salt, for use in the manufacture of a medicament for the treatment of a condition responsive to activation of the adenosine $A_{2A}$ receptor, particularly an inflammatory or obstructive airways disease.

The agents of the invention may be administered by any appropriate route, e.g., orally, for example, in the form of a tablet or capsule; parenterally, for example, intravenously; by inhalation, for example, in the treatment of inflammatory or obstructive airways disease; intranasally, for example, in the treatment of allergic rhinitis; topically to the skin, for example, in the treatment of atopic dermatitis; or rectally, for example, in the treatment of inflammatory bowel disease.

In a further aspect, the invention also provides a pharmaceutical composition comprising a compounds of formula (I), in free form or in the form of a pharmaceutically acceptable salt, optionally together with a pharmaceutically acceptable diluent or carrier therefor. The composition may contain a co-therapeutic agent, such as an anti-inflammatory, bronchodilatory, antihistamine or antitussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, for example, a hydro-fluoro-alkane (HFA) propellant, such as HFA134a or HFA227 or a mixture of these, and may contain one or more co-solvents known in the art, such as ethanol (up to 20% by weight), and/or one or more surfactants such as oleic acid or sorbitan trioleate, and/or one or more bulking agents, such as lactose. When the composition comprises a dry powder formulation, it preferably contains, for example, the compounds of formula (I) having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, for example, the compound of formula (I) either dissolved, or suspended, in a vehicle containing water, a co-solvent, such as ethanol or propylene glycol and a stabilizer, which may be a surfactant.

The invention includes (A) a compounds of formula (I) in inhalable form, e.g., in an aerosol or other atomisable composition or in inhalable particulate, e.g., micronised, form, (B) an inhalable medicament comprising a compounds of formula (I) in inhalable form; (C) a pharmaceutical product comprising a compounds of formula (I) in inhalable form in association with an inhalation device; and (D) an inhalation device containing a compounds of formula (I) in inhalable form.

Dosages of compounds of formula (I) employed in practising the present invention will of course vary depending, for example, on the particular condition to be treated, the effect desired and the mode of administration. In general, suitable daily dosages for administration by inhalation are of the order of 0.005-10 mg, while for oral administration suitable daily doses are of the order of 0.05-100 mg.

The invention is illustrated by the following Examples.

EXAMPLES

A compounds of formula X are shown in the following table. Methods of preparing such a compound is described hereinafter.

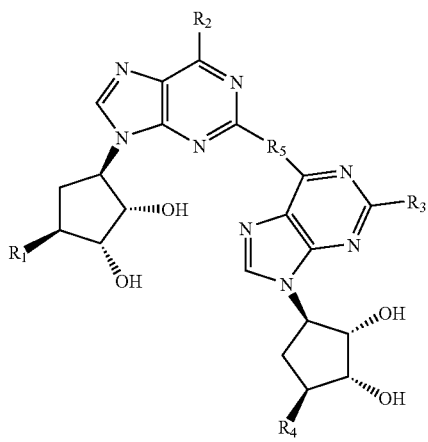

(X)

| Ex. | Structure |
|---|---|
| 1 | 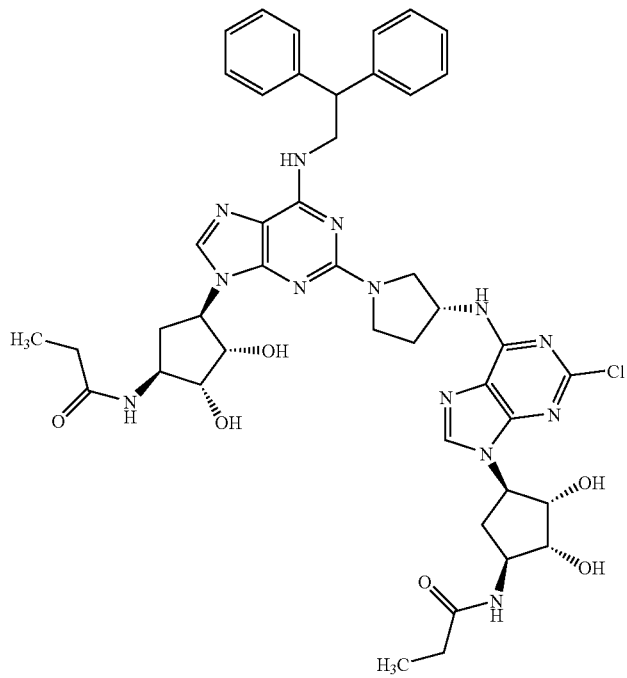 |

2
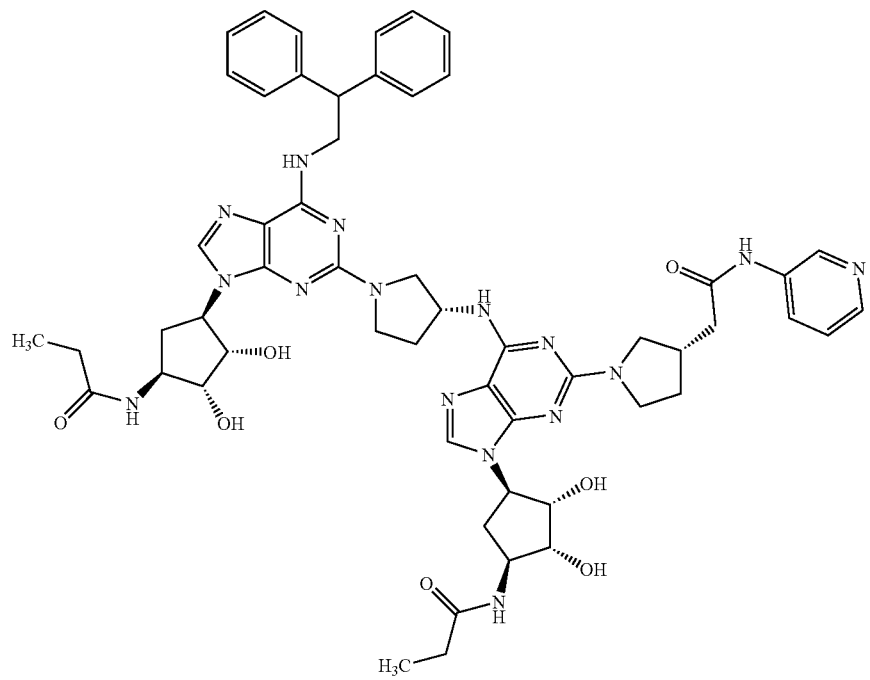
3
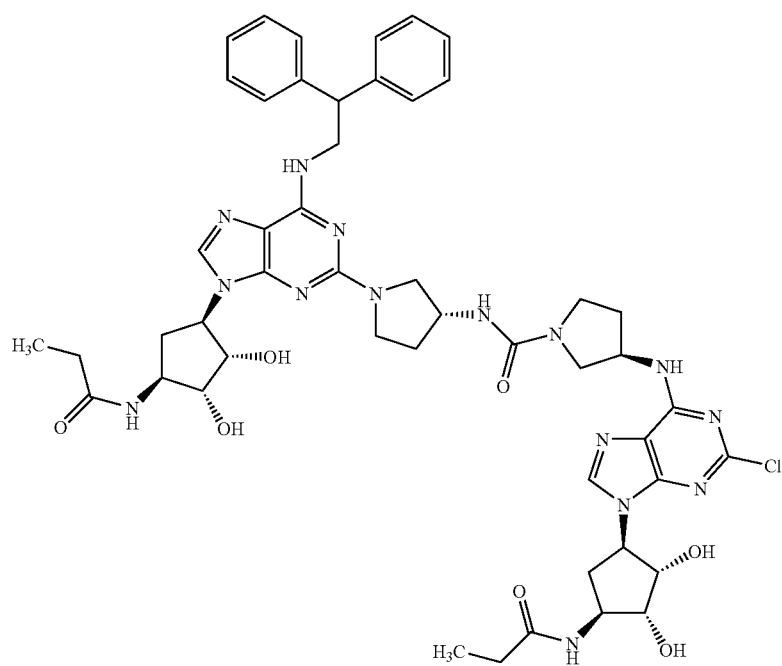

4
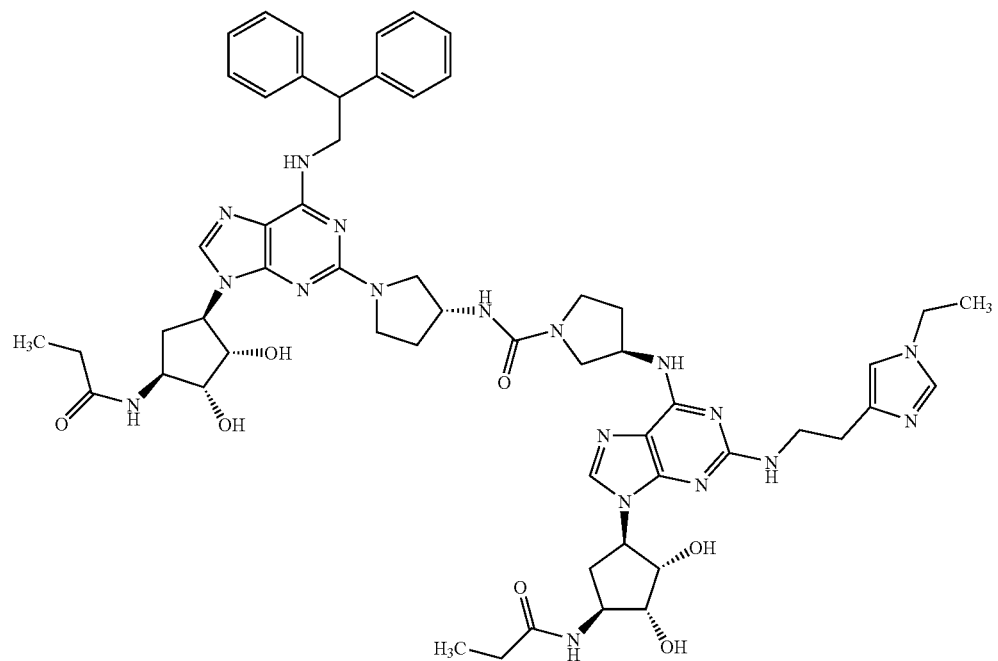
5
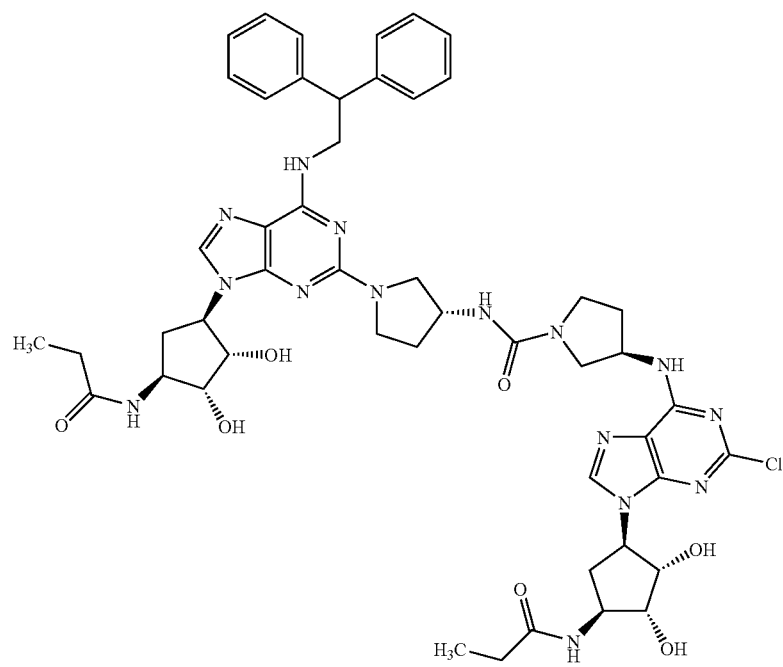

6
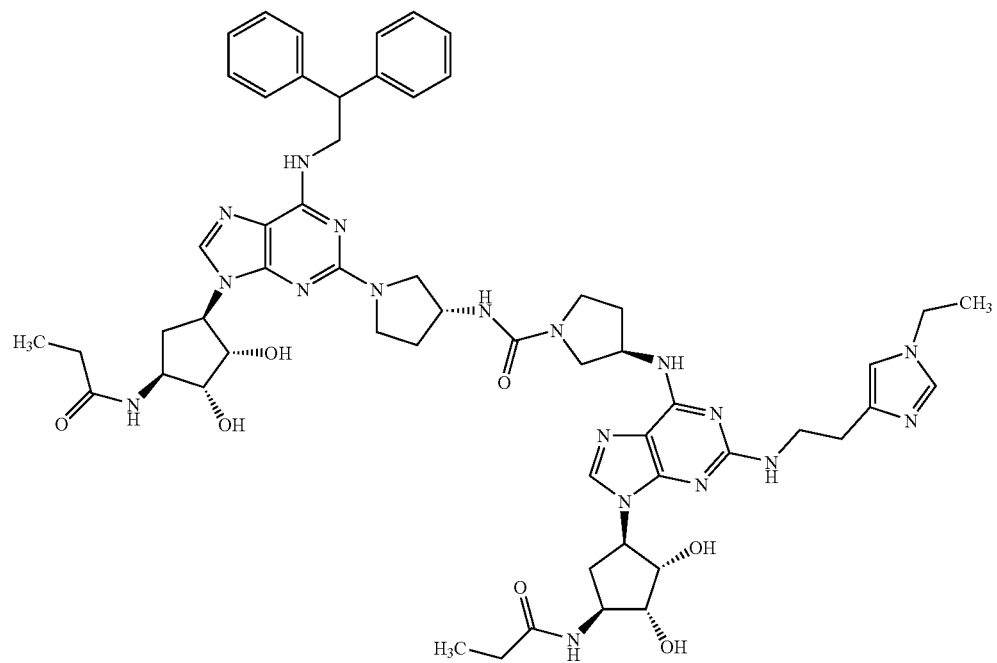
7
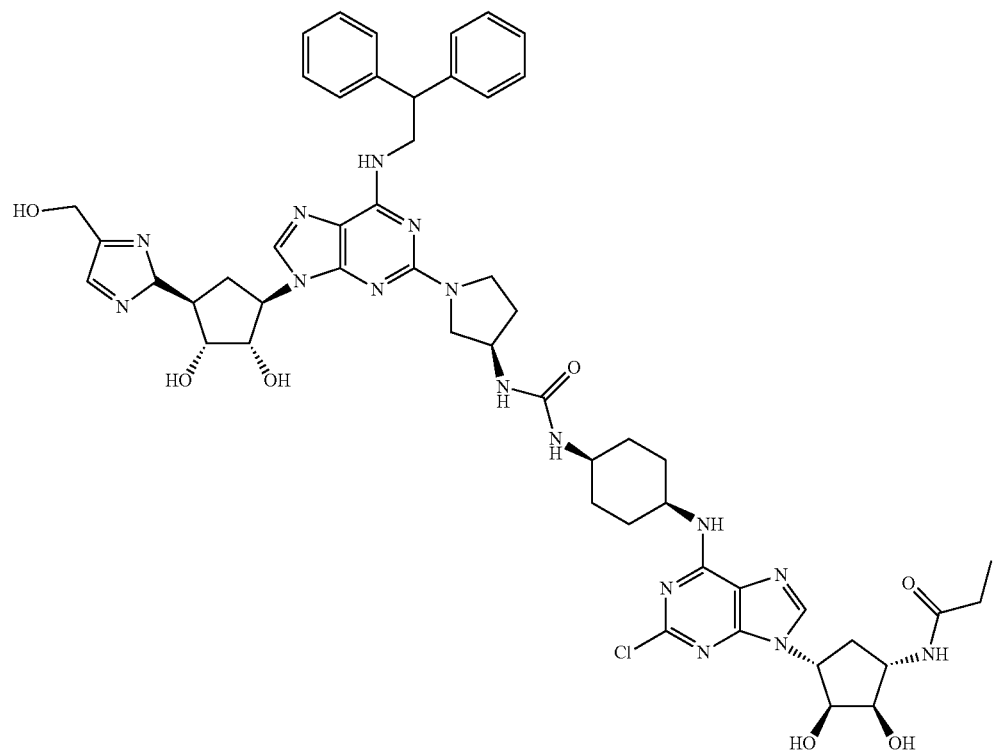

-continued
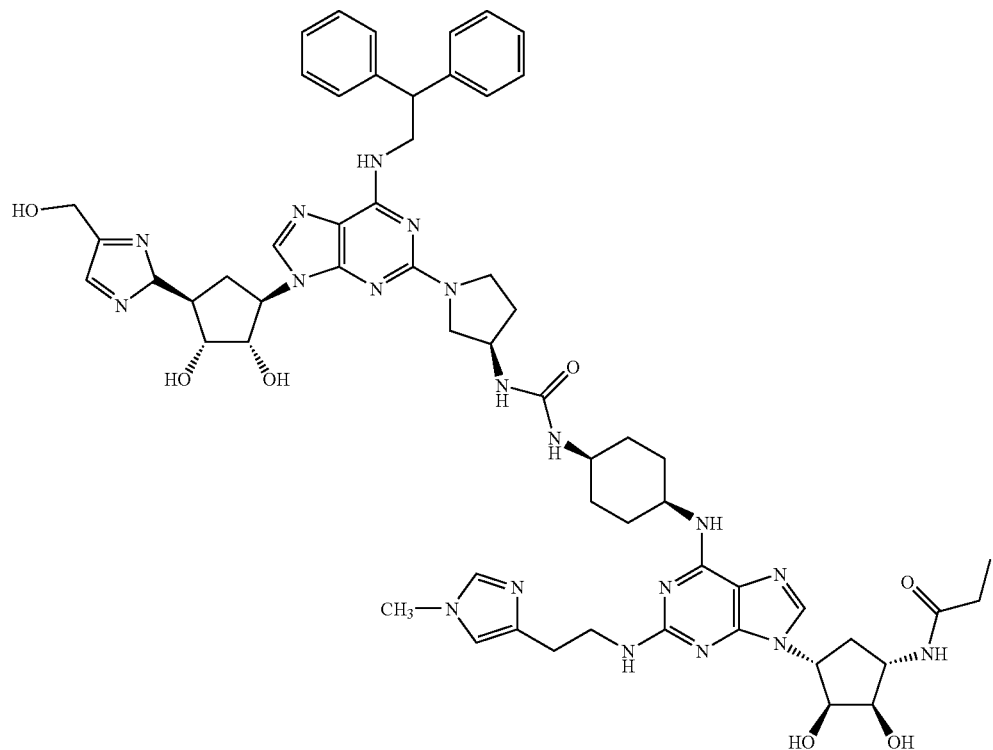
| Ex | R₁ | R₂ | R₃ | R₄ | R₅ |
|---|---|---|---|---|---|
| 1 | H₃C-C(=O)-NH- | diphenyl-CH-CH₂-NH-CH₃ | —Cl | H₃C-C(=O)-NH- | pyrrolidine-NH |
| 2 | H₃C-C(=O)-NH- | diphenyl-CH-CH₂-NH-CH₃ | pyrrolidine-NH-C(=O)-NH-pyridyl | H₃C-C(=O)-NH- | pyrrolidine-NH |
| 3 | H₃C-C(=O)-NH- | diphenyl-CH-CH₂-NH-CH₃ | —Cl | H₃C-C(=O)-NH- | pyrrolidine-NH-C(=O)-pyrrolidine-NH |

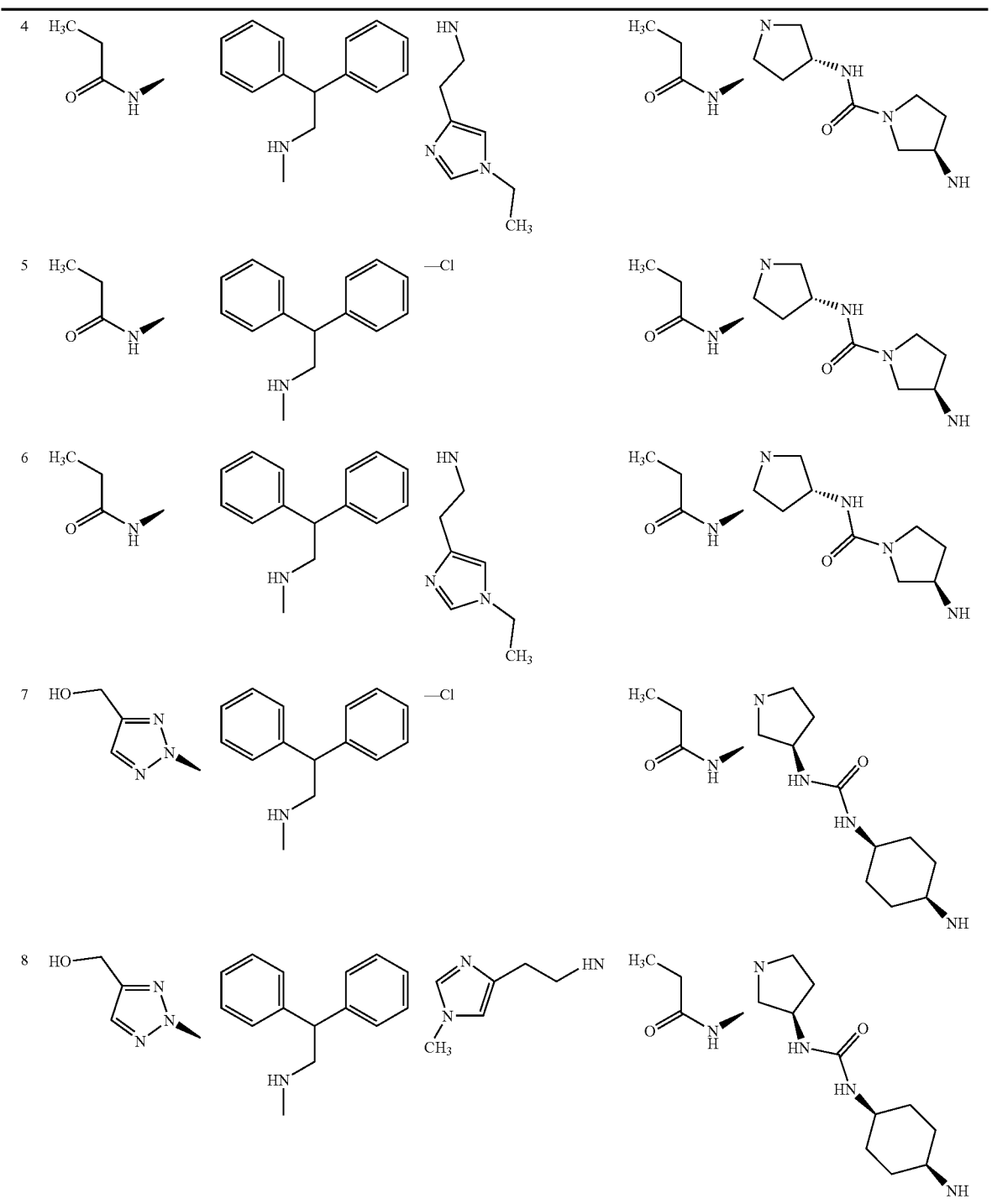

Preparation of Intermediates

Abbreviations used are as follows:

| | |
|---|---|
| CDI | 1,1'-Carbonyldiimidazole |
| DCM | Dichloromethane |
| DEAD | Diethyl Azodicarboxylate |
| DIPEA | Diisopropylethylamine |
| DMF | Dimethylformamide |
| DMSO | Dimethyl Sulfoxide |
| EDCI | 1-Ethyl-3-(3'-dimethylaminopropyl) carbodiimide |
| EtOAc | Ethyl Acetate |
| HPLC | High Performance Liquid Chromatography |
| HCl | Hydrochloric Acid |
| LCMS | Liquid Chromatographic Mass Spectroscopy |

| | |
|---|---|
| MeOH | Methanol |
| NMP | n-Methyl Pyrrolidone |
| NMO | N-Methylmorpholine N-Oxide |
| TEA | Triethylamine |
| TFA | Trifluoroacetic acid |
| THF | Tetrahydrofuran |

The following intermediates of formula (A)

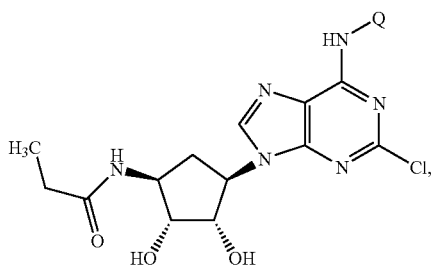

are shown in Table 1 below, their method of preparation being described hereinafter.

TABLE 1

| Intermediate | Q | M/s MH+ |
|---|---|---|
| AA | ![diphenylethyl] | 521 |
| AB | ![benzyl-methyl-CH2OH] | 475 |
| AC | ![bis(4-hydroxyphenyl)propyl] | 553 |

Intermediate AA

N-{(1S,2R,3S,4R)-4-[2-Chloro-6-(2,2-diphenyl-ethylamino)-purin-9-yl]-2,3-dihydroxy-cyclopentyl}-propionamide Step AA1 (1S,4R)-4-(2,6-Dichloro-purin-9-yl)-cyclopent-2-enol 2,6-Dichloropurine (10 g, 52.90 mmol), (1S,4R)-cis 4-acetoxy-2-cyclopenten-1-ol (10 g, 70.40 mmol), tris(dibenzylideneacetone)dipalladium(0) (3.20 g, 3.50 mmol) and polymer supported triphenylphosphine (3 mmol/g, 11.60 g, 35.00 mmol) are placed in an oven-dried flask under an atmosphere of argon. Dry deoxygenated THF (80 mL) is added and the reaction mixture is stirred gently for 5 minutes. TEA (20 mL) is added and the reaction mixture is stirred at 50° C. The reaction is shown to be complete by LCMS after 1 hour. The reaction mixture is allowed to cool, filtered and the solvent is removed in vacuo. The title compound is obtained after purification by flash column chromatography (silica, DCM/MeOH 25:1).

$^1$H NMR (CDCl$_3$, 400 MHz); 8.30 (s, 1H), 6.40 (m, 1H), 5.90 (m, 1H), 5.50 (m, 1H), 4.95 (m, 1H), 3.05 (m, 1H), 2.10 (m, 1H), MS (ES+) m/e 271 (MH$^+$).

Step AA2: Carbonic acid (1S,4R)-4-(2,6-dichloro-purin-9-yl)-cyclopent-2-enyl ester ethyl ester (1S,4R)-4-(2,6-Dichloro-purin-9-yl)-cyclopent-2-enol (9.5 g, 35.05 mmol) is placed in an oven-dried flask under an atmosphere of argon. Dry THF (200 mL) is added followed by dry pyridine (5.54 g, 70.1 mmol). Ethyl chloroformate (15.21 g, 140.2 mmol) is added slowly so that the temperature does not rise above 40° C. and the reaction mixture is stirred at room temperature. The reaction is shown to be complete by LCMS after 1 hour. The solvent is removed in vacuo and the residue is partitioned between DCM (200 mL) and water (200 mL). The organic layer is washed with water (150 mL) and brine (150 mL), dried over MgSO$_4$, filtered and the solvent is removed in vacuo. The title compound is obtained after crystallisation from MeOH.

$^1$H NMR (CDCl$_3$, 400 MHz); 8.20 (s, 1H), 6.45 (m, 1H), 6.25 (m, 1H), 5.75 (m, 1H), 5.70 (m, 1H), 4.25 (q, 2H), 3.20 (m, 1H), 2.05 (m, 1H), 1.35 (t, 3H), MS (ES+) m/e 343 (MH$^+$).

Step AA3: Di-Boc-[(1S,4R)-4-(2,6-dichloro-purin-9-yl)-cyclopent-2-enyl]-amine

Carbonic acid (1S,4R)-4-(2,6-dichloro-purin-9-yl)-cyclopent-2-enyl ester ethyl ester (2.5 g, 7.29 mmol), di-t-butyl-iminodicarboxylate (1.74 g, 8.02 mmol), and triphenylphosphine (0.29 g, 1.09 mmol) are placed in an oven-dried flask under an atmosphere of argon. Dry deoxygenated THF (30 ml) is added followed by tris(dibenzylideneacetone)dipalladium(0) (0.33 g, 0.36 mmol) and the reaction mixture is stirred at room temperature. The reaction is shown to be complete by LCMS after 3 hours. The solvent is removed in vacuo and the title compound is obtained after purification by flash column chromatography (silica, EtOAc/iso hexane 4:1).

$^1$H NMR (CDCl$_3$, 400 MHz); 8.70 (s, 1H), 6.20 (m, 1H), 5.85 (m, 1H), 5.80 (m, 1H), 5.40 (m, 1H), 3.20 (m, 1H), 2.15 (m, 1H), 1.55 (s, 18H), MS (ES+) m/e 470 (MH$^+$).

Step AA4: (1S,2R,3S,5R)-3-(Di-Boc-amino)-5-(2,6-dichloro-purin-9-yl)-cyclopentane-1,2-diol A mixture comprising di-Boc-[(1S,4R)-4-(2,6-dichloro-purin-9-yl)-cyclopent-2-enyl]-amine (1.30 g, 2.77 mmol) (1.49 g, 3.17 mmol), methane sulphonamide (0.30 g, 3.17 mmol) and AD-mix-α (6.75 g, 1.5 g/mmol) in t-butanol/water (20 mL of a 1:1 mixture) is treated with osmium tetroxide (1.5 mL, 4% w/w in water). After stirring vigorously at room temperature overnight, the reaction mixture is partitioned between EtOAc and water. The organic portion is separated, washed with water, brine, dried (MgSO$_4$) and concentrated in vacuo to yield the title compound which is used in the next step without further purification.

$^1$H NMR (CDCl$_3$, 400 MHz); 8.35 (s, 1H), 4.80 (m, 1H), 4.70 (m, 1H), 4.50 (m, 1H), 3.85 (m, 1H), 3.75 (m, 1H), 3.10 (m, 1H), 2.75 (m, 1H), 2.55 (m, 1H), 1.55 (s, 18H), MS (ES+) m/e 504 (MH$^+$).

Step AA5: (1S,2R,3S,5R)-3-Amino-5-(2,6-dichloro-purin-9-yl)-cyclopentane-1,2-diol trifluoroacetate A solution of (1S,2R,3S,5R)-3-(di-Boc-amino)-5-(2,6-dichloro-purin-9-yl)-cyclopentane-1,2-diol (0.55 g, 1.09 mmol) in DCM (4 mL) is treated with TFA (2 mL) and stirred at room temperature. After 2 hours, the solvent is removed in vacuo to yield the title compound which is used in the next step without further purification. MS (ES+) m/e 304 (MH$^+$).

Step AA6: N-[(1S,2R,3S,4R)-4-(2,6-Dichloro-purin-9-yl)-2,3-dihydroxy-cyclopentyl]-propionamide A solution of (1S,2R,3S,5R)-3-amino-5-(2,6-dichloro-purin-9-yl)-cyclopentane-1,2-diol trifluoroacetate (0.304 g, 1.0 mmol) in THF (10 mL) is treated with DIPEA (0.387 g, 3.0 mmol) followed by propionyl chloride (0.093 g, 1.0 mmol). After stirring at room temperature for 2 hours, the solvent is removed in vacuo and the title compound is obtained after purification by reverse phase column chromatography (Isolute™ C18, 0-100% acetonitrile in water-0.1% TFA). MS (ES+) m/e 360 (MH$^+$).

Step AA7: N-{(1S,2R,3S,4R)-4-[2-Chloro-6-(2,2-diphenyl-ethylamino)-purin-9-yl]-2,3-dihydroxy-cyclopentyl}-propionamide N-[(1S,2R,3S,4R)-4-(2,6-dichloro-purin-9-yl)-2,3-dihydroxy-cyclopentyl]-propionamide (160 mg, 0.44 mmol) is dissolved in THF (5 mL) under an atmosphere of argon. DIPEA (69 mg, 0.53 mmol) is added followed by 2,2-diphenylethylamine (96 mg, 0.49 mmol) and the reaction mixture is stirred at 50° C. The reaction is shown to be complete by LCMS after 2 hours. The solvent is removed in vacuo and the title compound is obtained after purification by reverse phase column chromatography (Isolute™ C18, 0-100% acetonitrile in water-0.1% TFA).

$^1$H NMR (MeOD, 400 MHz); 8.00 (s, 1H), 7.40-7.15 (m, 10H), 4.75 (m, 1H), 4.60 (m, 1H), 4.50 (m, 1H), 4.20 (m, 3H), 3.95 (m, 1H), 2.85 (m, 1H), 2.40 (q, 2H), 2.10 (m, 1H), 1.20 (t, 3H), MS (ES+) m/e 521 (MH$^+$).

Intermediate AA may also be prepared using the following process:

Step AAI1: {2-Chloro-9-[(1R,4S)-4-(di-Boc-amino)-cyclopent-2-enyl]-9H-purin-6-yl}-(2,2-diphenyl-ethyl)-amine (1S,2R,3S,5R)-3-(di-Boc-amino)-5-(2,6-dichloro-purin-9-yl)-cyclopentane-1,2-diol (13.0 g, 27.66 mmol) is dissolved in THF (250 mL) under an atmosphere of argon. DIPEA (4.28 g, 33.19 mmol) is added followed by 2,2-diphenylethylamine (6.0 g, 30.43 mmol) and the reaction mixture is stirred at 50° C. The reaction is shown to be complete by LCMS after 18 hours. The solvent is removed in vacuo and the reaction mixture is partitioned between dichloromethane (250 mL) and 0.1 M HCl (250 mL). The organic layer is washed with water (200 mL) and brine (200 mL), dried over MgSO$_4$, filtered and the solvent is removed in vacuo to give the title compound.

$^1$H NMR (CDCl$_3$, 400 MHz); 8.05 (s, 1H), 7.30-7.10 (m, 10H), 6.00 (m, 1H), 5.70 (m, 2H), 5.60 (m, 1H), 5.20 (m, 1H), 4.30 (m, 1H), 4.20 (m, 1H), 3.65 (m, 1H), 3.05 (m, 1H), 2.00 (m, 1H), 1.70 (m, 1H), 1.40 (s, 18H), MS (ES+) m/e 631 (MH$^+$).

Step AAI2: (1R,2S,3R,5S)-3-[2-Chloro-6-(2,2-diphenyl-ethylamino)-purin-9-yl]-5-(di-Boc-amino)-cyclopentane-1,2-diol The title compound is prepared analogously to (1S,2R,3S,5R)-3-(di-Boc-amino)-5-(2,6-dichloro-purin-9-yl)-cyclopentane-1,2-diol by replacing di-Boc-[(1S,4R)-4-(2,6-dichloro-purin-9-yl)-cyclopent-2-enyl]-amine with {2-chloro-9-[(1R,4S)-4-(di-Boc-amino)-cyclopent-2-enyl]-9H-purin-6-yl}-(2,2-diphenyl-ethyl)-amine.

$^1$H NMR (MeOD, 400 MHz); 8.05 (s, 1H), 7.35-7.15 (m, 10H), 4.70-4.55 (m, 4H), 4.50 (m, 1H), 4.35 (m, 1H), 4.20 (m, 2H), 2.55 (m, 1H), 2.45 (m, 1H), 1.60 (s, 18H).

Step AAI3: (1S,2R,3S,5R)-3-Amino-5-[2-chloro-6-(2,2-diphenyl-ethylamino)-purin-9-yl]-cyclopentane-1,2-diol trifluoroacetate (1R,2S,3R,5S)-3-[2-Chloro-6-(2,2-diphenyl-ethylamino)-purin-9-yl]-5-(di-Boc-amino)-cyclopentane-1,2-diol (10.3 g, 15.50 mmol) is dissolved in DCM (50 mL). TFA (25 mL) is added and the reaction mixture is stirred at room temperature. The reaction is shown to be complete by LCMS after 2 hours. The solvent is removed in vacuo to give the title compound.

$^1$H NMR (MeOD, 400 MHz); 7.90 (s, 1H), 7.30-7.10 (m, 10H), 4.65 (m, 1H), 4.50 (m, 1H), 4.40 (m, 1H), 4.20 (m, 1H), 4.10 (m, 2H), 3.50 (m, 1H), 2.75 (m, 1H), 2.15 (m, 1H), MS (ES+) m/e 465 (MH$^+$).

Step AAI4: N-{(1S,2R,3S,4R)-4-[2-Chloro-6-(2,2-diphenyl-ethylamino)-purin-9-yl]-2,3-dihydroxy-cyclopentyl}-propionamide (1S,2R,3S,5R)-3-Amino-5-[2-chloro-6-(2,2-diphenyl-ethylamino)-purin-9-yl]-cyclopentane-1,2-diol TFA (9.50 g, 16.42 mmol) and DIPEA (6.36 g, 49.27 mmol) are placed in a flask with dry THF (150 mL). Propionyl chloride (1.52 g, 16.42 mmol) is added dropwise and the reaction mixture is stirred at room temperature. The reaction is shown to be complete by LCMS after 1 hour. The solvent is removed in vacuo and the residue is partitioned between DCM (250 mL) and water (250 mL). The organic layer is washed with water (200 mL) and brine (200 mL), dried over MgSO$_4$, filtered and the solvent is removed in vacuo. The solid is recrystallized from 1,2-dichloroethane to give the title compound.

$^1$H NMR (MeOD, 400 MHz); 8.00 (s, 1H), 7.40-7.15 (m, 10H), 4.75 (m, 1H), 4.60 (m, 1H), 4.50 (m, 1H), 4.20 (m, 3H), 3.95 (m, 1H), 2.85 (m, 1H), 2.40 (q, 2H), 2.10 (m, 1H), 1.20 (t, 3H), MS (ES+) m/e 521 (MH$^+$).

Intermediate AB

N-{(1S,2R,3S,4R)[2-Chloro-6-((S)-1-hydroxymethyl-2-phenyl-ethylamino)-purin-9-yl]-2,3-dihydroxy-cyclopentyl}-propionamide trifluoroacetate Step AB1: [(1S,4R)-4-(2,6-Dichloro-purin-9-yl)-cyclopent-2-enyl]-propionyl-carbamic acid tert-butyl ester The title compound is prepared analogously to di-Boc-[(1S,4R)-4-(2,6-dichloro-purin-9-yl)-cyclopent-2-enyl]-amine (by replacing di-t-butyliminodicarboxylate with propionyl-carbamic acid tert-butyl ester.

Step AB2: [(1S,2R,3S,4R)-4-(2,6-Dichloro-purin-9-yl)-2,3-dihydroxy-cyclopentyl]-propionyl-carbamic acid tert-butyl ester A mixture comprising [(1S,4R)-4-(2,6-dichloro-purin-9-yl)-cyclopent-2-enyl]-propionyl-carbamic acid tert-butyl ester (6.54 g, 15.8 mmol), methane sulphonamide (1.46 g, 15.3 mmol) and AD-mix-α (23 g, 1.5 g/mmol) in t-butanol/water (80 mL of a 1:1 mixture) is treated with osmium tetroxide (3.5 mL, 4% w/w in water). After stirring vigorously at room temperature for 72 hours, the reaction mixture is partitioned between EtOAc and water. The organic portion is separated, washed with water, brine, dried (MgSO$_4$) and concentrated in vacuo. The resulting residue is triturated with methanol to afford the title compound. MS (ES+) m/e 460 (MH$^+$).

Step AB3: N-{(1S,2R,3S,4R)-4-[2-Chloro-6-((S)-1-hydroxymethyl-2-phenyl-ethylamino)-purin-9-yl]-2,3-dihydroxy-cyclopentyl}-propionamide trifluoroacetate A solution comprising [(1S,2R,3S,4R)-4-(2,6-dichloro-purin-9-yl)-2,3-dihydroxy-cyclopentyl]-propionyl-carbamic acid tert-butyl ester (0.5 g, 1.1 mmol), DIPEA (0.227 mL, 1.3 mmol), (S)-2-amino-3-phenyl-propan-1-ol (0.181 mg, 1.2 mmol) in 1,2-dichloroethane (3 mL) is heated at 50° C. overnight. 0.1 M HCl (10 mL) is added to the reaction mixture and following agitation, the organic portion is separated and treated with TFA (1 mL). After standing at room temperature for 2 hours, the solvent is removed in vacuo to yield the title compound. MS (ES+) m/e 475.2 (MH+).

Intermediate AC

This compound is prepared analogously to Intermediate AB by replacing (S)-2-amino-3-phenyl-propan-1-ol with 4,4'-(2-aminoethylidene)bisphenol (prepared according to the preparation of Schelkun et al., *Bioorg Med Chem Lett*, Vol. 9, pp. 2447-2452 (1999) MS (ES+) m/e 553.2 (MH+).

Intermediate B

N-{(1S,2R,3S,4R)-4-[2-((R)-3-Amino-pyrrolidin-1-yl-6-(2,2-diphenyl-ethylamino)-purin-9-yl]-2,3-dihydroxy-cyclopentyl}-propionamide dihydrochloride Step B1: {(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-carbamic acid tert-butyl ester
A reaction mixture comprising N-{(1S,2R,3S,4R)-4-[2-chloro-6-(2,2-diphenyl-ethylamino)-purin-9-yl]-2,3-dihydroxy-cyclopentyl}-propionamide (2.5 g, 4.80 mmol) and (3R)-(+)-(3-Boc-amino)pyrrolidine (2.5 g, 13.6 mmol) in DMSO (8 mL) is heated at 100° C. overnight. Purification of the product by reverse phase column chromatography (Isolute™ C18, 0-20% acetonitrile in water-0.1% TFA) yields the title compound. MS (ES+) m/e 521.4 (MH+).
Step B2: N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-propionamide dihydrochloride
{(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-carbamic acid tert-butyl ester (ca 4.80 mmol) is dissolved in 1.25 M HCl in MeOH (60 mL). After stirring at room temperature for 3 days, the solvent is removed in vacuo to yield the title compound. MS (ES+) m/e 571.24 (MH+).

Intermediate C

N-{(1S,2R,3S,4R)-4-[2-Chloro-6-(2,2-diphenyl-ethylamino)-purin-9-yl]-2,3-dihydroxy-cyclopentyl}-2-hydroxy-acetamide Step C1: Acetic acid {(1S,2R,3S,4R)-4-[2-chloro-6-(2,2-diphenyl-ethylamino)-purin-9-yl]-2,3-dihydroxy-cyclopentylcarbamoyl}-methyl ester
A suspension of (1S,2R,3S,5R)-3-amino-5-[2-chloro-6-(2,2-diphenyl-ethylamino)-purin-9-yl]-cyclopentane-1,2-diol dihydrochloride (Intermediate AAl13) (250 mg, 0.46 mmol) in dry THF (10 mL) is treated with TEA (0.188 g, 1.86 mmol) followed by acetoxyacetylchloride (0.064 g, 0.46 mmol) and then stirred at room temperature for 30 minutes. The solvent is removed in vacuo and the solvent is partitioned between DCM and 0.1 M HCl. The organic portion is separated and washed with brine, dried (MgSO$_4$) and concentrated in vacuo to afford the title product. MS (ES+) m/e 565.38 (MH+).
Step C2: N-{(1S,2R,3S,4R)-4-[2-Chloro-6-(2,2-diphenyl-ethylamino)-purin-9-yl]-2,3-dihydroxy-cyclopentyl}-2-hydroxy-acetamide
To a suspension of acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (0.2 g, 0.35 mmol) in MeOH (10 mL) is added potassium carbonate (0.098 g, 0.7 mmol) and the reaction mixture is stirred at room temperature for 1 hour. The solvent is removed in vacuo and the solvent is partitioned between DCM and water. The organic portion is separated, dried (MgSO$_4$) and concentrated in vacuo to afford the title product. MS (ES+) m/e 522.4/524.5 (MH+).

Intermediate D

{1-[(1S,4R)-4-(2,6-Dichloro-purin-9-yl)cyclopent-2-enyl]-1H-pyrazol-4-yl}-methanol A mixture comprising carbonic acid (1S,4R)-4-(2,6-dichloro-purin-9-yl)-cyclopent-2-enyl ester ethyl ester (Intermediate AA2) (1.00 g, 2.92 mmol), (1H-pyrazol-4-yl)-methanol (preparation shown below) (0.34 g, 3.50 mmol) and triphenyl phosphine (0.115 g, 0.44 mmol) in deoxygenated THF (10 mL) under an inert atmosphere of argon is treated with tris(dibenzylideneacetone)dipalladium(0) (0.13 g, 0.15 mmol) and stirred at 50° C. for 1 hour. The solvent is removed in vacuo and the crude product is purified by chromatography on silica eluting with MeOH/DCM (1:25) to yield the title compound.
Preparation of (1H-pyrazol-4-yl)-methanol
4-Ethylpyrazole carboxylate (10 g, 71.40 mmol) is placed in an oven-dried flask under an atmosphere of argon. Dry THF (100 mL) is added followed by the dropwise addition of lithium aluminum hydride (1 M in THF, 100 mL, 100 mmol). Once the addition is complete the reaction mixture is stirred at 50° C. The reaction is shown to be complete by NMR after 4 hours. The reaction mixture is cooled on an ice-bath and the reaction mixture is quenched with water (3.8 mL) then 15% sodium hydroxide (3.8 mL) and finally water again (11.4 mL). The solvent is removed in vacuo and the solid is placed in a Soxhlet apparatus. THF is refluxed through the system for 24 hours. The solvent is removed in vacuo to give the title compound.
$^1$H NMR (MeOD, 400 MHz); 7.60 (s, 2H), 4.55 (s, 2H).

Intermediate E

[4-((R)-3-Pyrrolidin-3-ylureido)-cyclohexyl]-carbamic acid tert-butyl ester

Step E1: (4-tert-Butoxycarbonylamino-cyclohexyl)-carbamic acid phenyl ester
Phenyl chloroformate (1 eq.) is added dropwise to a solution of pyridine/DCM. The reaction mixture is cooled to 0° C. and a solution of (4-amino-cyclohexyl)-carbamic acid tert-butyl ester (1 eq.) in DCM is added dropwise. The reaction mixture is stirred at room temperature for 1 hour. The reaction mixture is partitioned between (0.2 M) HCl$_{(aq)}$ and DCM. The organics are washed with water, saturated sodium hydrogen carbonate solution and brine. The combined organics are dried (MgSO$_4$), filtered and reduced in vacuo to yield the title compound.
Step E2: {4-[3-((R)-1-Benzyl-pyrrolidin-3-yl)-ureido]-cyclohexyl}-carbamic acid tert-butyl ester
A solution of (4-tert-butoxycarbonylamino-cyclohexyl)-carbamic acid phenyl ester (1 eq.) and (R)-1-benzyl-pyrrolidin-3-ylamine (1 eq.) in MeOH is heated using microwave radiation at 100° C. for 30 minutes. The resulting solution is purified by reverse phase column chromatography (Isolute™ C18, 0-100% acetonitrile in water 0.1% HCl) to afford the title compound.

Step E3: [4-((R)-3-Pyrrolidin-3-ylureido)-cyclohexyl]-carbamic acid tert-butyl ester To a solution of {4-[3-((R)-1-benzyl-pyrrolidin-3-yl)-ureido]-cyclohexyl}-carbamic acid tert-butyl ester in ethanol under an inert atmosphere of argon is added palladium hydroxide on carbon. The reaction mixture is purged with argon and placed under an atmosphere of hydrogen overnight. The mixture is filtered and the catalyst washed with ethanol. The organic portions are combined and concentrated in vacuo to yield the title compound.

Intermediate F

[(R)-1-((R)-Pyrrolidin-3-ylcarbamoyl)-pyrrolidin-3-yl]-carbamic acid tert-butyl ester This compound is prepared analogously to Intermediate E by replacing (4-amino-cyclohexyl)-carbamic acid tert-butyl ester with (R)-pyrrolidin-3-yl-carbamic acid tert-butyl ester.

Intermediate F

[(R)-1-((R)-Pyrrolidin-3-ylcarbamoyl)-pyrrolidin-3-yl]-carbamic acid tert-butyl ester may also be prepared using the following process

Step F1: ((R)-1-Benzyl-pyrrolidin-3-yl)-carbamic acid 4-nitro-phenyl ester

4-Nitro-phenyl chloroformate (1 eq.) is added dropwise to a solution of pyridine/DCM (1:5) at 0° C. The reaction mixture is kept at 0° C. and a solution of (R)-1-benzyl-pyrrolidin-3-ylamine (1 eq.) in DCM is added dropwise. The reaction mixture is stirred at room temperature overnight. The reaction mixture is partitioned between (0.2 M) HCl$_{(aq)}$ and DCM. The organics are washed with water, saturated sodium hydrogen carbonate solution and brine. The combined organics are dried (MgSO$_4$), filtered and reduced in vacuo to yield the title compound. MS (ES+) m/e 342.10 (MH$^+$).

Step F2: [(R)-1-((R)-1-Benzyl-pyrrolidin-3-ylcarbamoyl)-pyrrolidin-3-yl]-carbamic acid tert-butyl ester A solution of ((R)-1-benzyl-pyrrolidin-3-yl)-carbamic acid 4-nitro-phenyl ester (1 eq.) and (3R)-(+)-3-(Boc-amino)pyrrolidine in MeOH is heated using microwave radiation at 100° C. for 1 hour. The reaction mixture is reduced in vacuo. The resulting oil is dissolved in DCM and isocyanate resin (3 eq.) is added and shaken overnight. The resin was filtered off and the DCM was removed in vacuo to yield the title compound. MS (ES+) m/e 299.21 (MH$^+$).

Step F3: [(R)-1-((R)-Pyrrolidin-3-ylcarbamoyl)-pyrrolidin-3-yl]-carbamic acid tert-butyl ester To a solution of [(R)-1-((R)-1-benzyl-pyrrolidin-3-ylcarbamoyl)-pyrrolidin-3-yl]-carbamic acid tert-butyl ester in ethanol under an inert atmosphere of argon is added palladium hydroxide on carbon. The reaction mixture is purged with nitrogen and placed under an atmosphere of hydrogen overnight. The mixture is filtered and the catalyst washed with ethanol. The organic portions are combined and concentrated in vacuo. The resulting brown oil is purified by column chromatography (Isolute™ Si, 2% MeOH in DCM) yield the title compound. MS (ES+) m/e 389.25 (MH$^+$).

Intermediate G

{4-[3-(4-Amino-cyclohexyl)-ureido]-cyclohexyl}-carbamic acid tert-butyl ester This compound is prepared analogously to Intermediate E by replacing (R)-1-benzyl-pyrrolidin-3-ylamine (Step E2) with (4-amino-cyclohexyl)-carbamic acid benzyl ester.

Intermediate H

[1-((R)-Pyrrolidin-3-ylcarbamoyl)-piperidin-4-yl]-carbamic acid tert-butyl ester This compound is prepared analogously to Intermediate F by replacing (3R)-(+)-3-(BOC-amino)pyrrolidine with Piperidin-4-yl-carbamic acid tert-butyl ester in step F2.

Intermediate I

{4-[4-(Pyrrolidin-3-ylamino)-[1,3,5]triazin-2-ylamino]-cyclohexyl}-carbamic acid tert-butyl ester

Step I1: (R)-3-[4-(4-tert-Butoxycarbonylamino-cyclohexylamino)-[1,3,5]triazin-2-ylamino]-pyrrolidine-1-carboxylic acid allyl ester (R)-3-Amino-pyrrolidine-1-carboxylic acid allyl ester (1 eq.) is dissolved in DCM. The reaction mixture is cooled to 0° C. and a solution of 2,4-dichloro-[1,3,5]triazine (1 eq.) in DCM is added dropwise. The reaction mixture is stirred at room temperature for 2 hours. The reaction mixture is re-cooled to 0° C. and a solution of (4-amino-cyclohexyl)-carbamic acid tert-butyl ester (1 eq.) in DCM is added dropwise. The reaction mixture is stirred at room temperature overnight. The reaction mixture is partitioned between (0.2 M) HCl$_{(aq)}$ and DCM. The organics are washed with water, saturated NaHCO$_{3(aq)}$ and brine. The combined organics are dried (MgSO$_4$), filtered and reduced in vacuo, to yield the title compound.

Step I2: {4-[4-((R)-Pyrrolidin-3-ylamino)-[1,3,5]triazin-2-ylamino]-cyclohexyl}-carbamic acid tert-butyl ester Can be made from the product of Step 1 following Ref: Foms et al., *Tetrahedron Lett*, Vol. 44, No. 36, pp. 6907-6910 (2003). Using (R)-3-[4-(4-tert-butoxycarbonylamino-cyclohexylamino)-[1,3,5]triazin-2-ylamino]-pyrrolidine-1-carboxylic acid allyl ester instead of the resin-bound amine.

Preparation of Examples

Example 1

{(1S,2R,3S,4R)-4-[2-{(R)-3-[2-Chloro-9-((1R,2S,3R,4S)-2,3-dihydroxy-4-propionylamino-cyclopentyl)-9H-purin-6-ylamino]-pyrrolidin-1-yl}-6-(2,2-diphenyl-ethylamino)-purin-9-yl]-2,3-dihydroxy-cyclopentyl}-propionamide Step 1: [(1S,2R,3S,4R)-4-(2-Chloro-6-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-ylamino}-purin-9-yl)-2,3-dihydroxy-cyclopentyl]-dicarbamic acid tert-butyl ester (1S,2R,3S,5R)-3-(di-Boc-amino)-5-(2,6-dichloro-purin-9-yl)-cyclopentane-1,2-diol (Intermediate AA4) (52 mg, 0.10 mmol) and N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (Intermediate B) (58 mg, 0.10 mmol) are suspended in ⁱPrOH (1 mL). DIPEA (0.089 mL, 0.51 mmol) is added and the reaction mixture is heated using microwave radiation at 100° C. for 1 hour. The reaction mixture is partitioned between water and EtOAc and the organic portion is dried (MgSO₄), filtered and reduced in vacuo. Purification by reverse phase column chromatography (Isolute™ C18, 0-100% acetonitrile in water) affords the title compound. (MH+ 1038/1040).

Step 2: N-{(1S,2R,3S,4R)-4-[2-{(R)-3-[9-((1R,2S,3R,4S)-4-Amino-2,3-dihydroxy-cyclopentyl)-2-chloro-9H-purin-6-ylamino]-pyrrolidin-1-yl}-6-(2,2-diphenyl-ethylamino)-purin-9-yl]-2,3-dihydroxy-cyclopentyl}-propionamide

[(1S,2R,3S,4R)-4-(2-Chloro-6-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-ylamino}-purin-9-yl)-2,3-dihydroxy-cyclopentyl]-dicarbamic acid tert-butyl ester (39 mg, 0.038 mmol) is dissolved in MeOH (1 mL) and (4 M) HCl in dioxane (1 mL) is added. The reaction mixture is stirred at room temperature overnight. The reaction mixture is reduced in vacuo yield the title compound. (MH+ 838).

Step 3: N-{(1S,2R,3S,4R)-4-[2-{(R)-3-[2-Chloro-9-((1R,2S,3R,4S)-2,3-dihydroxy-4-propionylamino-cyclopentyl)-9H-purin-6-ylamino]-pyrrolidin-1-yl}-6-(2,2-diphenyl-ethylamino)-purin-9-yl]-2,3-dihydroxy-cyclopentyl}-propionamide N-{(1S,2R,3S,4R)-4-[2-{(R)-3-[9-((1R,2S,3R,4S)-4-Amino-2,3-dihydroxy-cyclopentyl)-2-chloro-9H-purin-6-ylamino]-pyrrolidin-1-yl}-6-(2,2-diphenyl-ethylamino)-purin-9-yl]-2,3-dihydroxy-cyclopentyl}-propionamide (32 mg, 0.038 mmol) and TEA (0.016 mL, 0.113 mmol) are suspended in THF (0.5 mL). MeOH (0.5 mL) is added to aid solubility. Propionic acid chloride (0.0035 mL, 0.040 mmol) is added and the reaction mixture is stirred at room temperature overnight. The reaction mixture is reduced in vacuo and purified by reverse phase column chromatography (Isolute™ C18, 0-100% acetonitrile in water-0.1% TFA) to yield the title compound (MH+ 894/895).

Example 2

N-{(1S,2R,3S,4R)-4-[2-[(R)-3-[2-[(R)-3-(3-Pyridin-3-yl-ureido)-pyrrolidin-1-yl]-9-((1R,2S,3R,4S)-2,3-dihydroxy-4-propionylamino-cyclopentyl)-9H-purin-6-ylamino]-pyrrolidin-1-yl]-6-(2,2-diphenyl-ethylamino)-purin-9-yl]-2,3-dihydroxy-cyclopentyl}-propionamide N-{(1S,2R,3S,4R)-4-[2-{(R)-3-[2-Chloro-9-((1R,2S,3R,4S)-2,3-dihydroxy-4-propionylamino-cyclopentyl)-9H-purin-6-ylamino]-pyrrolidin-1-yl}-6-(2,2-diphenyl-ethylamino)-purin-9-yl]-2,3-dihydroxy-cyclopentyl}-propionamide (1 eq.) and 1-pyridin-3-yl-3-(R)-pyrrolidin-3-yl-urea (3 eq.) are dissolved in EtOH. The reaction mixture is refluxed at room temperature for 48 hours. The reaction mixture is reduced in vacuo and purified by reverse phase column chromatography (Isolute™ C18, 0-100% acetonitrile in water-0.1% TFA) to yield the title compound.

Examples 3-8 are prepared individually by the following methods described for multi-parallel synthesis.

Examples of the formula (I) are prepared in a multiparallel sequence of reactions as described below.

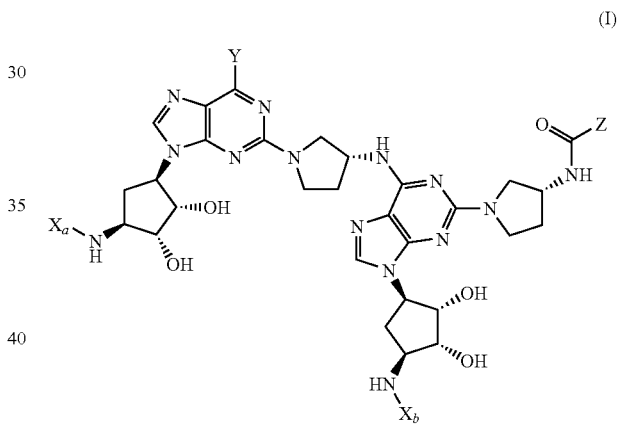

(I)

Scheme 1

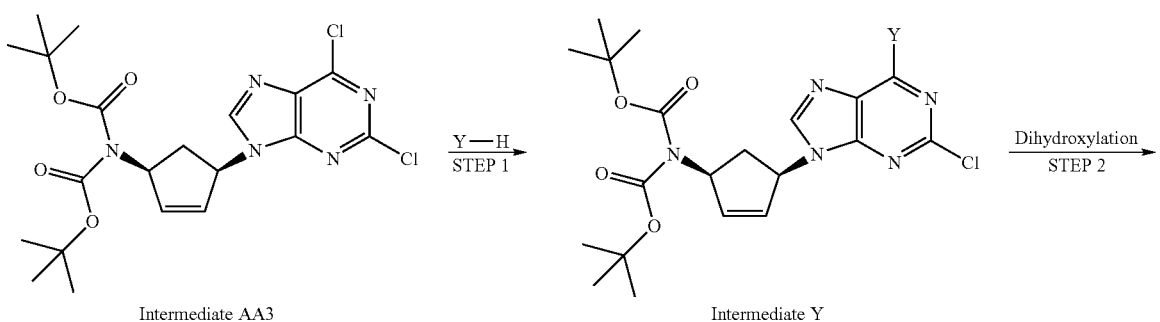

-continued
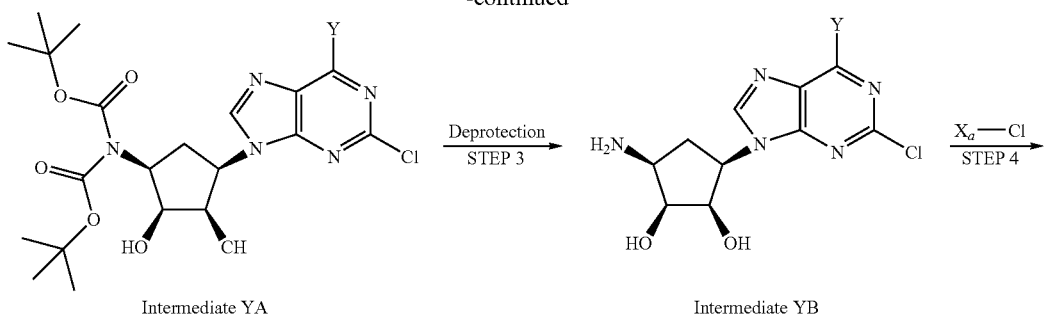
Intermediate YA → Deprotection STEP 3 → Intermediate YB → $X_a$—Cl STEP 4 →
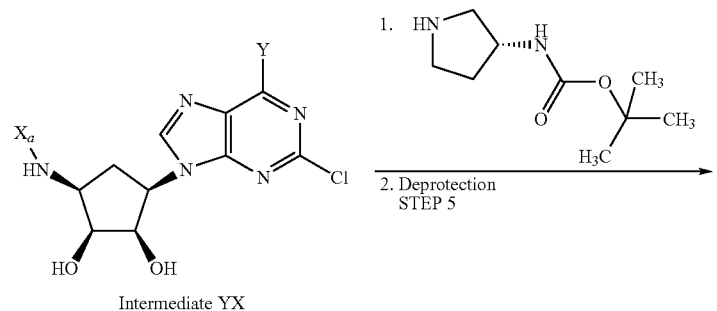
Intermediate YX
1. <img of pyrrolidine with NHBoc>
2. Deprotection STEP 5
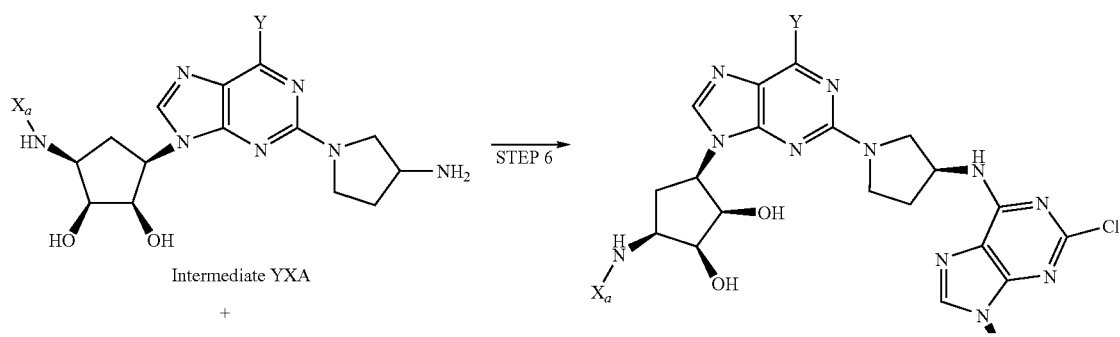
Intermediate YXA +
STEP 6 →
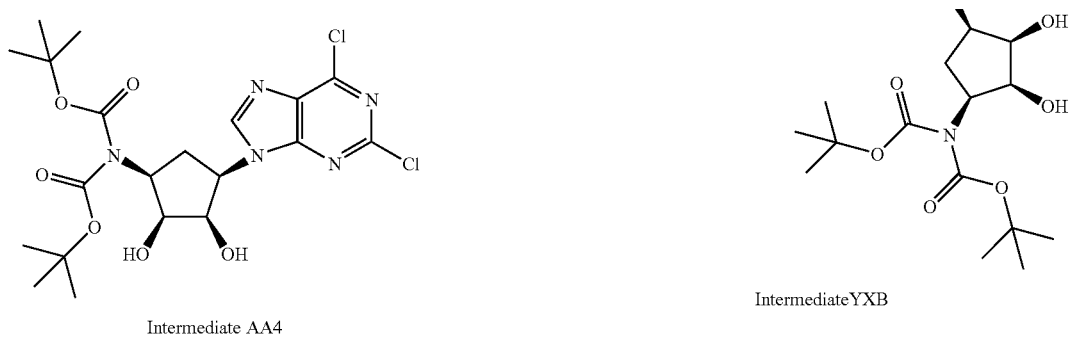
Intermediate AA4
Intermediate YXB
STEP 7
1. Deprotection
2. $X_b$—Cl

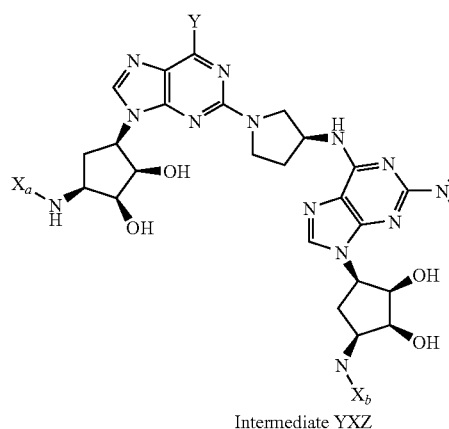

Intermediate YXZ

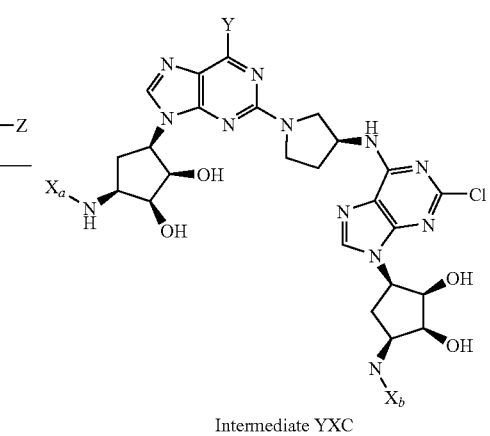

Intermediate YXC

Step 1:

Reaction of Intermediate AA3, in an analogous manner to that used in the preparation of Intermediate AAI1 by replacing diphenylethylamine with the appropriate amine, individually with the amines Y-H gives the Intermediate Y.

Amines Y-H

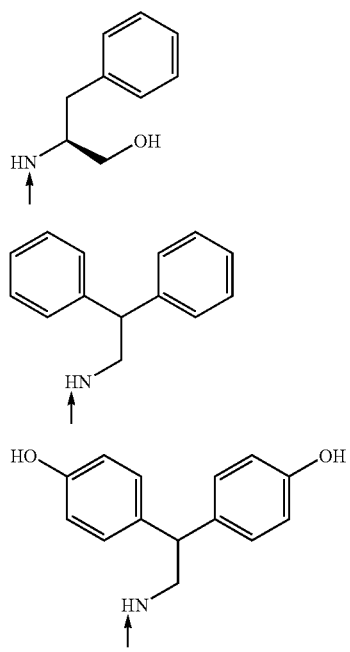

Y1

Y2

Y3

Step 2:

Reaction of Intermediates Y individually with either the dihydroxylating agent osmium tetroxide or ruthenium tetroxide gives the Intermediates YA.

Step 3:

Reaction of Intermediates YA, in an analogous manner to that used in the preparation of Intermediate AAI3 gives the Intermediates YB.

Step 4:

Reaction of Intermediates YB with the appropriate acid chloride, in an analogous manner to that used in the preparation of either Intermediate AAI4 (with propionyl chloride) or Intermediate C (with acetoxyacetylchloride) gives the Intermediates YX.

Intermediates YX

Where $X_a$=CH$_3$CH$_2$C(O)—, CH$_3$OC(O)—, HOCH$_2$C(O)—, HOCH(CH$_3$)C(O)—

Step 5:

Reaction of Intermediates YX with (3R)-(+)-(3-Boc-amino)pyrrolidine followed by deprotection in an analogous manner to that used in the preparation of Intermediate B gives the Intermediates YXA.

Steps 6 and 7:

Reaction of Intermediates YXA, in an analogous manner to that used to prepare Example 1, individually using the appropriate acid chlorides in Step 3 affords the Intermediates YXC.

Intermediates YXC

Where $X_b$=CH$_3$CH$_2$C(O)—, CH$_3$OC(O)—, HOCH$_2$C(O)—, HOCH(CH$_3$)C(O)—

Step 8:

Intermediates YXC are reacted in ethanol at reflux, or in DMSO at 90-110° C., for 18-24 hours individually with a 3-fold excess of the appropriate Intermediate Z. The examples or Formula (I) are isolated following purification by mass directed reversed phase chromatography.

Intermediate Z

Where

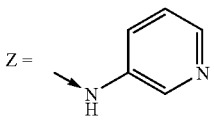

Z1

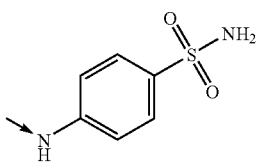

Z2

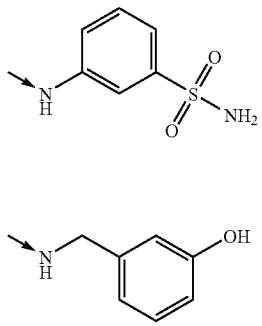
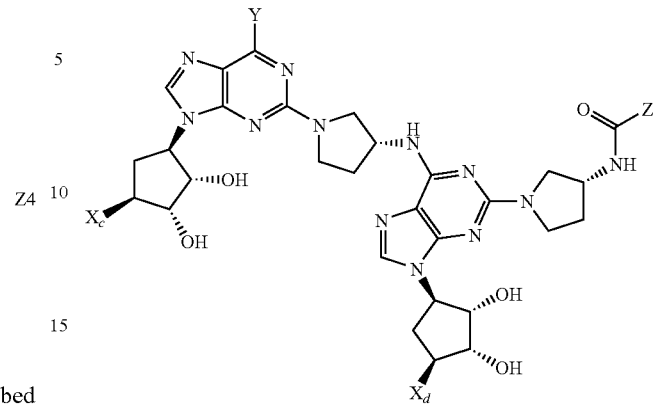
Examples of formula (II) can be prepared as described below in Scheme 2:
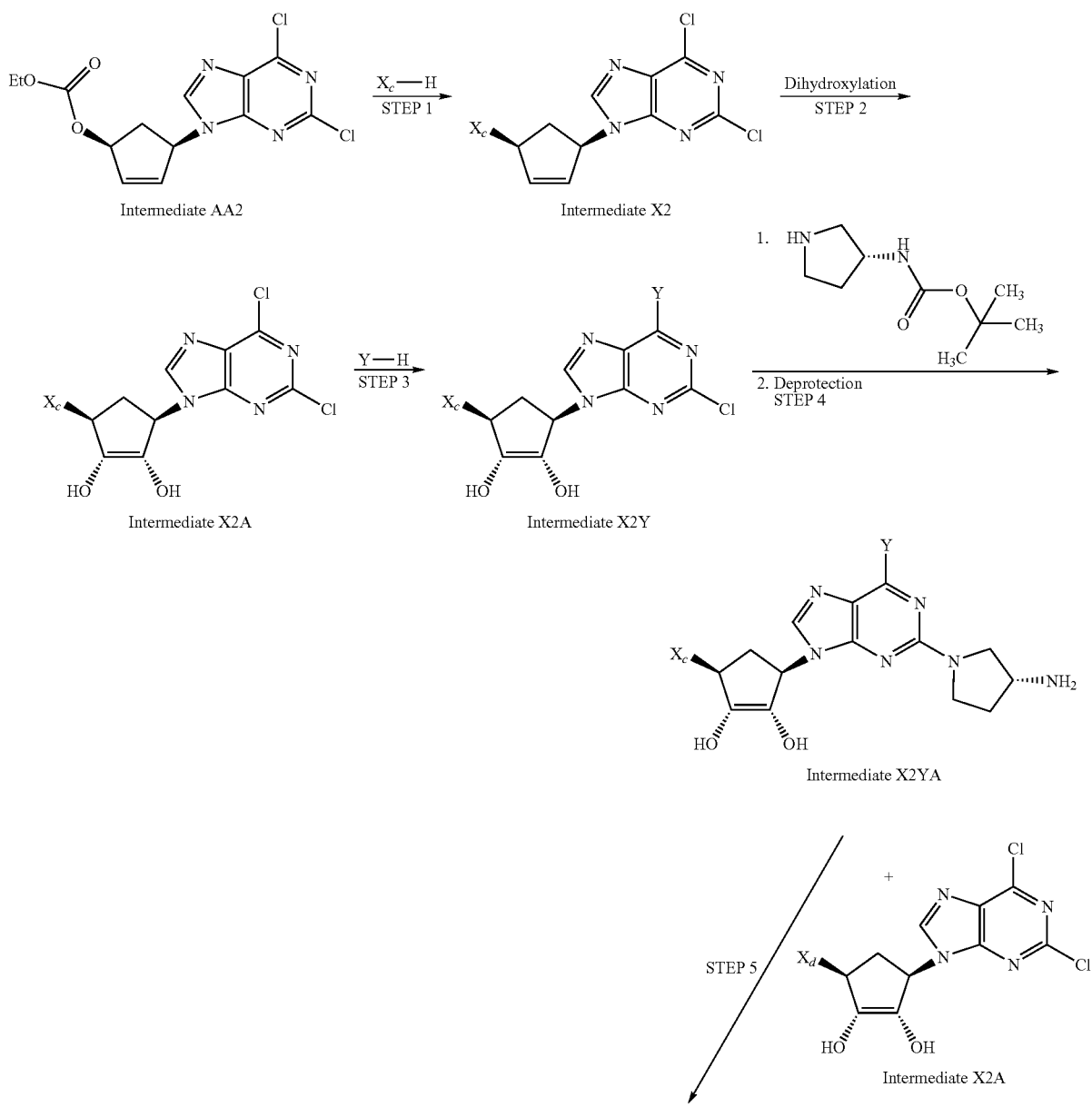

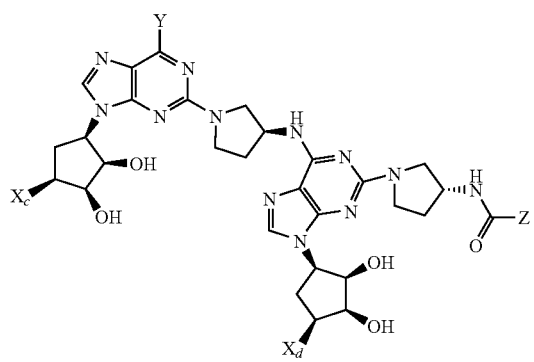 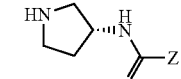 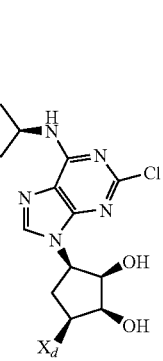

Intermediate X2YB

Step 1:
Reaction of Intermediate AA2, in an analogous manner to that used in the preparation of Intermediate D, by replacing (1H-pyrazol-4-yl)-methanol with the appropriate heterocycle, individually with the heterocycles $X_c$-H gives the Intermediates X2.

Heterocycles $X_c$-H

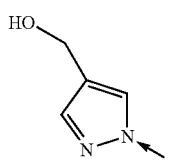

X1

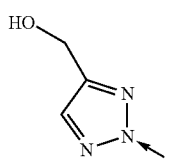

X2

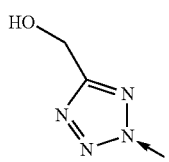

X3

Heterocycles X-H are prepared as follows:
X1 the preparation is described with Intermediate D.
X2-X3 are prepared following literature procedures.

Step 2:
Reaction of Intermediates X2, individually with either the dihydroxylating agent osmium tetroxide or ruthenium tetroxide gives the Intermediates X2A.

Step 3:
Reaction of Intermediates X2A, in an analogous manner to that used in the preparation of Intermediate AB, Step AB3 by replacing (S)-2-amino-3-phenyl-propan-1-ol with the appropriate amine, individually with the amines Y-H gives the Intermediates X2Y.

Step 4:
Intermediates X2Y are reacted with (3R)-(+)-(3-Boc-amino)pyrrolidine followed by deprotection in an analogous manner to that used in the preparation of Intermediate B gives the Intermediates Y2XA.

Step 5:
Reaction of Intermediates Y2XA in an analogous manner to that used to prepare [(1S,2R,3S,4R)-4-(2-chloro-6-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-ylamino}-purin-9-yl)-2,3-dihydroxy-cyclopentyl]-di-carbamic acid tert-butyl ester (Example 1, Step 1), individually using the corresponding Intermediate X2A affords the Intermediate X2YB.

Where $X_d$ is selected from

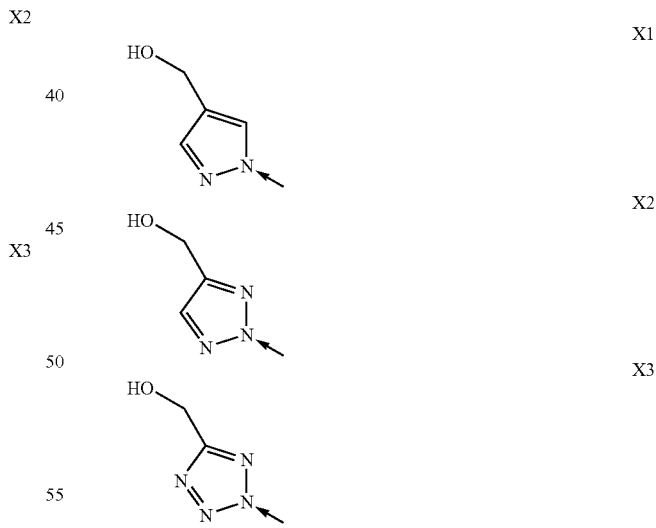

Step 6:
Intermediate X2YB are reacted in ethanol at reflux, or in DMSO at 90-110° C., for 18-24 hours individually with a 3-fold excess of the appropriate Intermediate Z (as described previously). The examples of formula (III) are isolated following purification by mass directed reversed phase chromatography.

Examples of the formula (III) are prepared as described below.

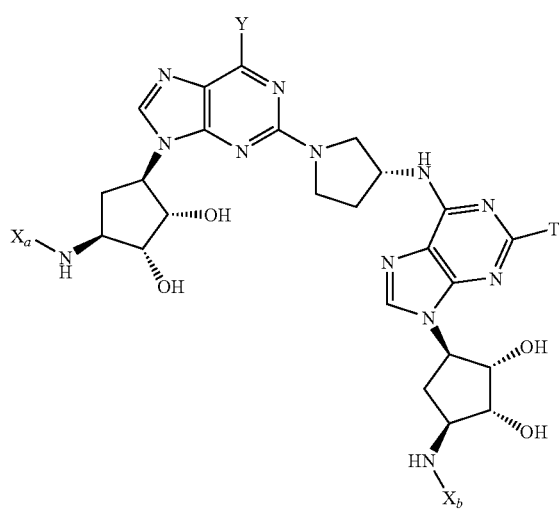
(III)
Scheme 3
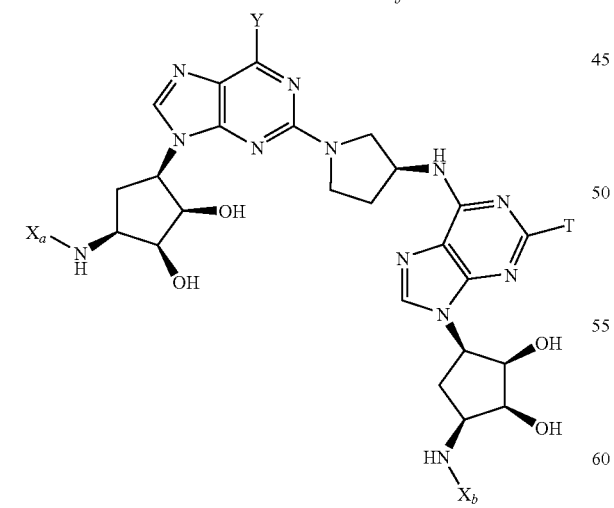
III
Intermediates YXC are reacted in acetonitrile/N-methyl-pyrrolidone in the presence of sodium iodide, triethylamine, individually with the amines T-H. Heating with microwave radiation at temperatures from 120-220° C. gives the series of Examples of formula (III).
Amines T-H
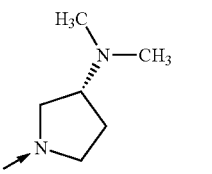
T1
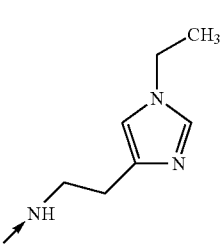
T2
T3
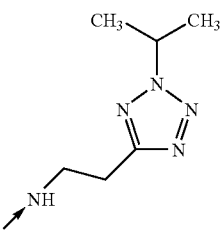
T4
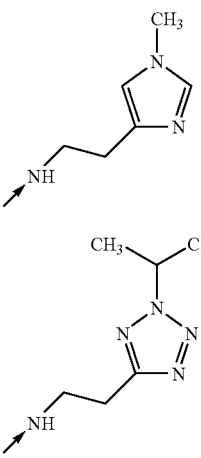
Examples of the formula (IV) are prepared as described below.
(IV)
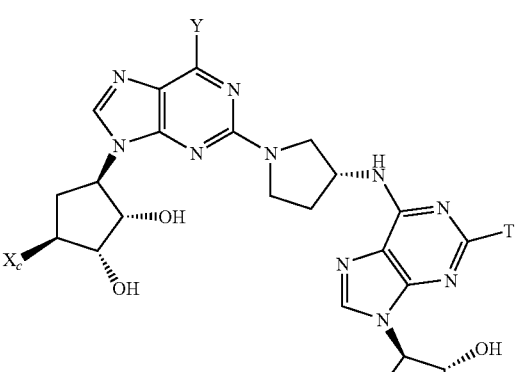

These examples are prepared from Intermediates X2YB in an analogous manner to that used to prepare Examples of formula (III).

Examples of the formula (V) are prepared as described below.

(V)

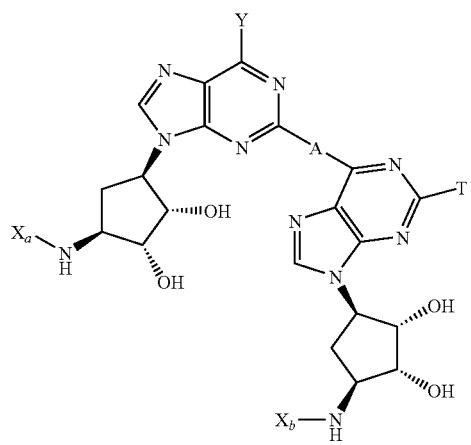

Scheme 4:

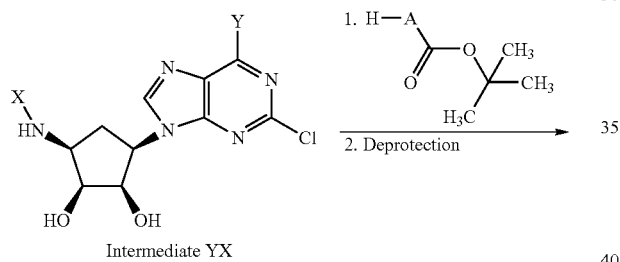

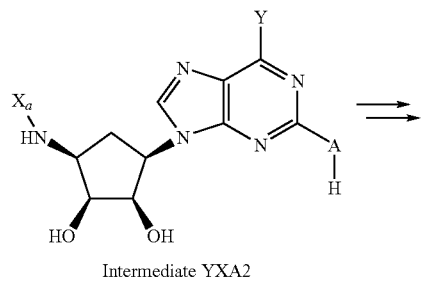

Intermediate YXA2

+

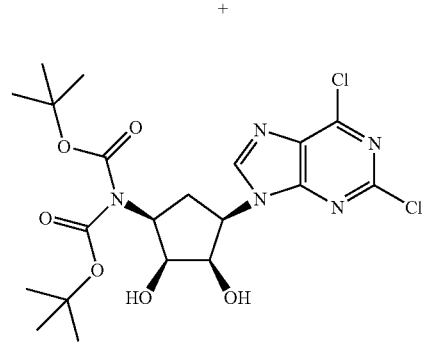

Intermediate AA4

-continued

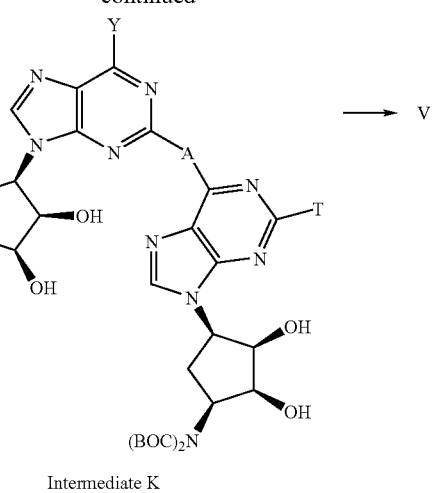

Intermediate K

These examples are prepared from Intermediates YXA2 analogously to examples of formula (III). Intermediates YXA2 are prepared from Intermediates YX in an analogous manner to that used in the preparation of Intermediate B by replacing (3R)-(+)-(3-Boc-amino)pyrrolidine with the appropriate Boc-protected amine (Boc)-A-H.

Boc-protected amine (Boc)-A-H:

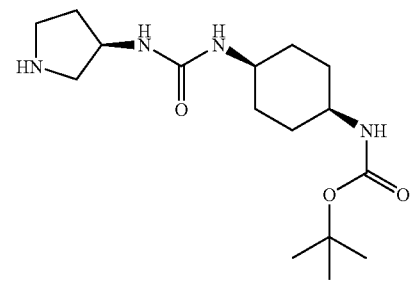

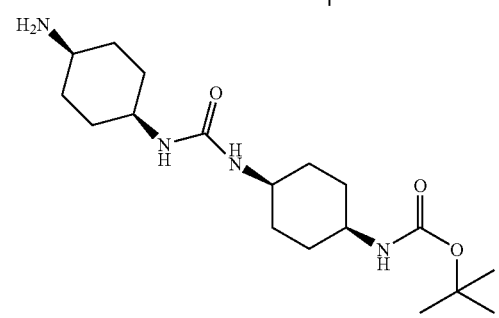

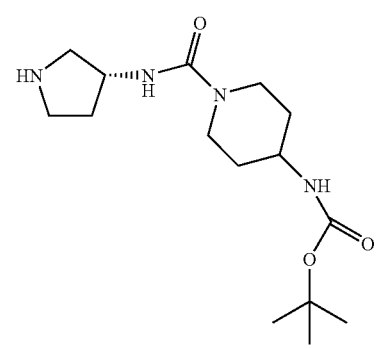

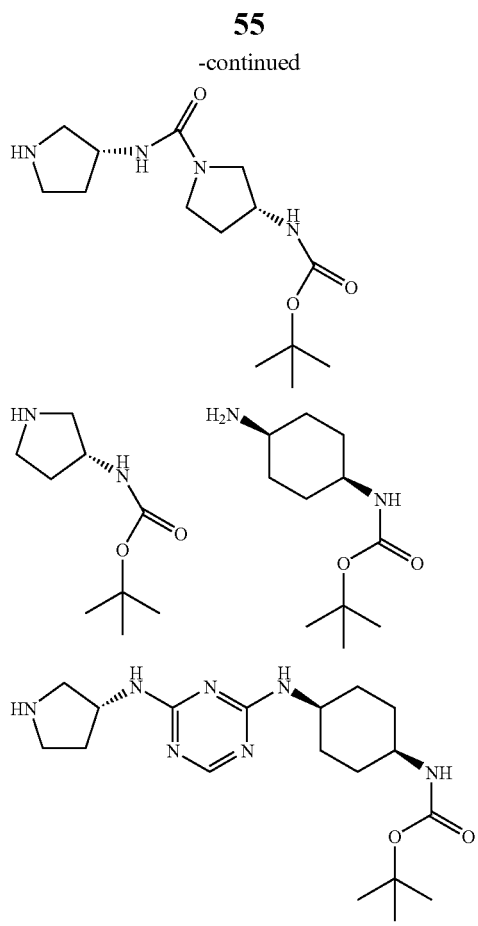
Resulting A Linkers:
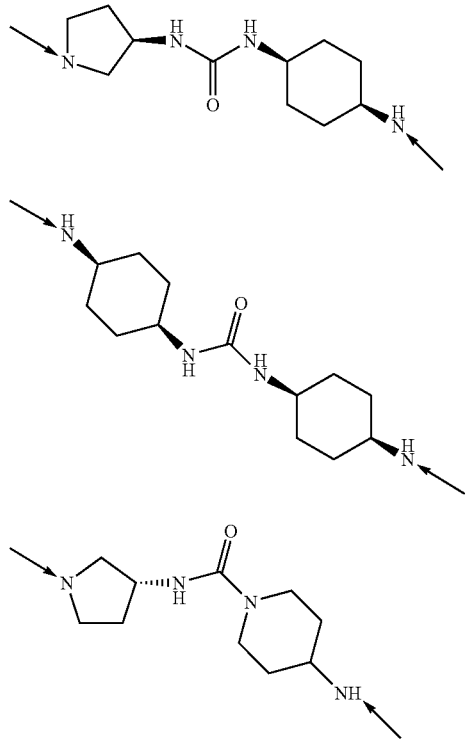
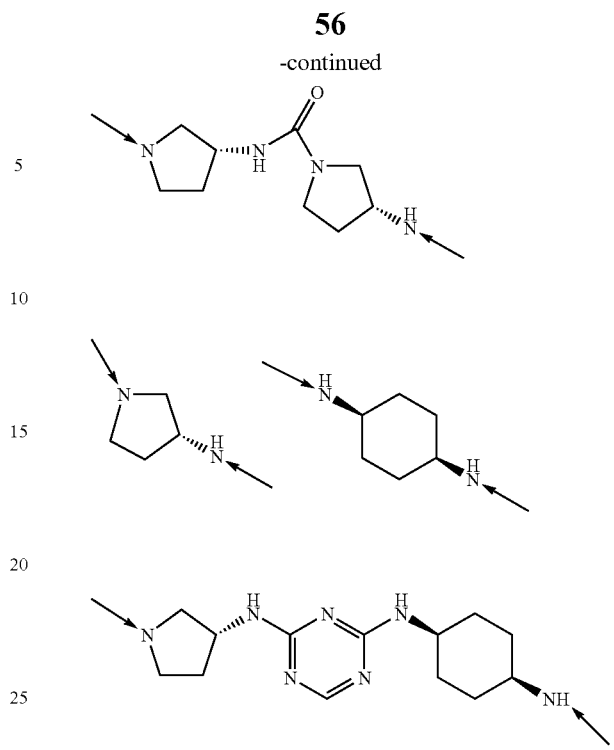
Intermediate K is converted to Example V in an analogues fashion to Example I.
Examples of the formula (VI) are prepared as described below.
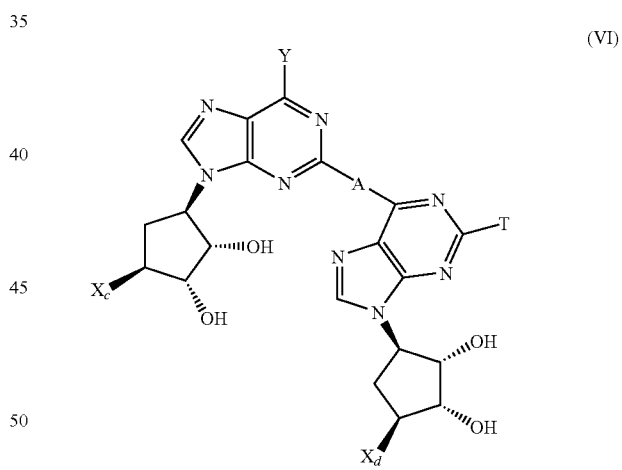
Scheme 5:
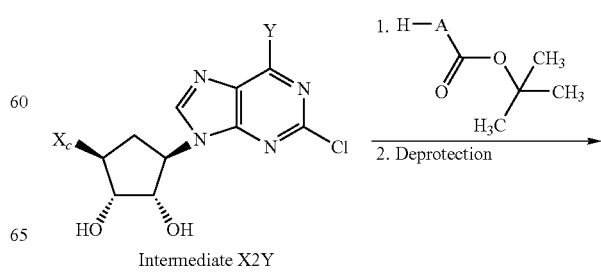
Intermediate X2Y

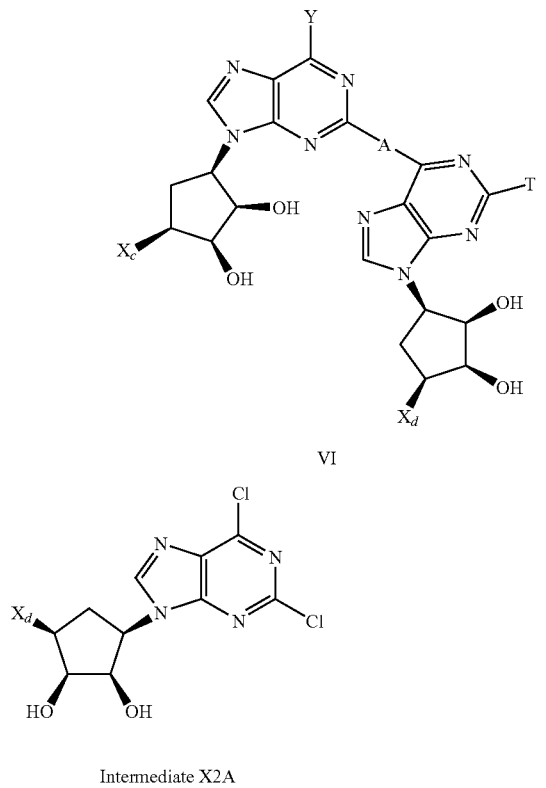

VI

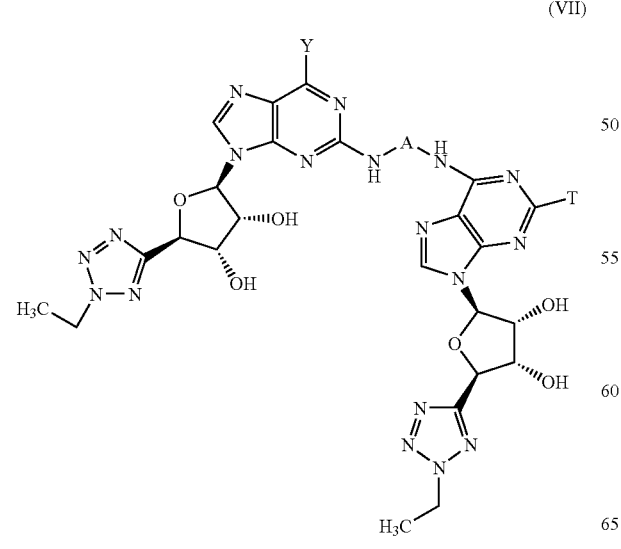

Intermediate X2A

These examples are prepared from Intermediates X2YA2 analogously to examples of formula (III). Intermediates X2YA2 are prepared from Intermediates X2Y in an analogous manner to that used in the preparation of Intermediate B by replacing (3R)-(+)-(3-Boc-amino)pyrrolidine with the appropriate Boc-protected amine (Boc)-A-H.

Ribose Examples

Examples of the formula (VII) are prepared as described below.

(VII)

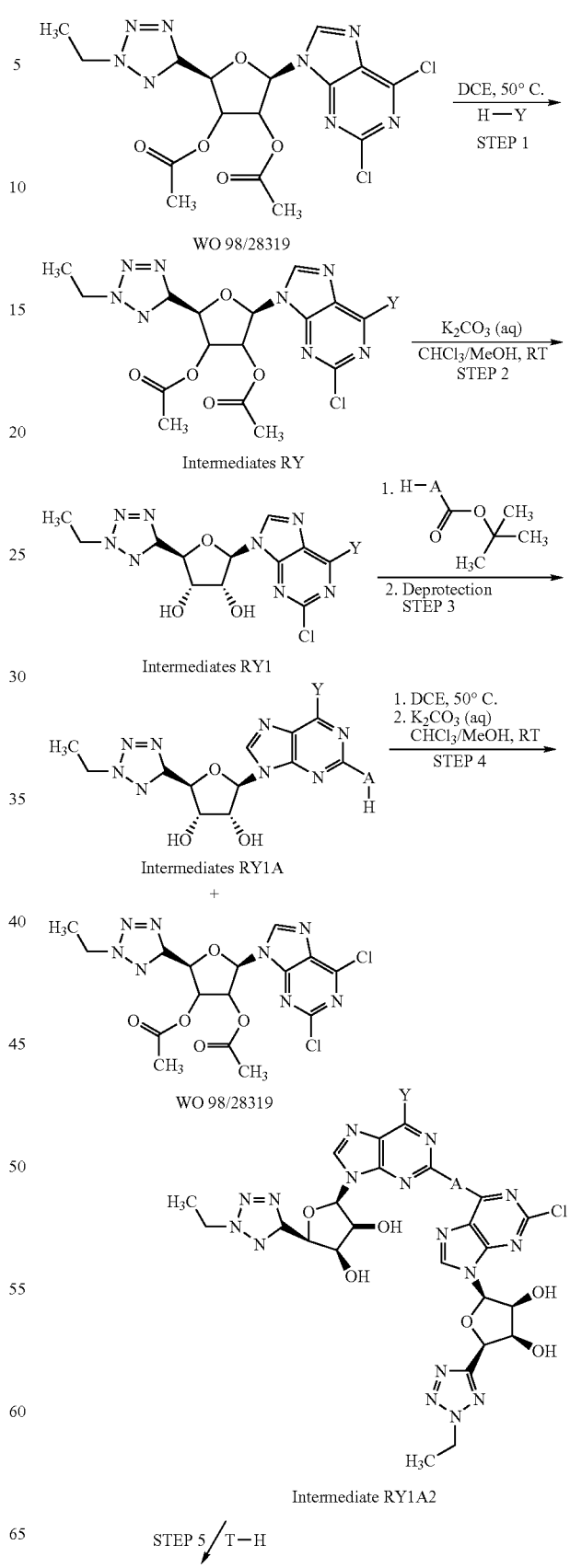

Scheme 6

-continued

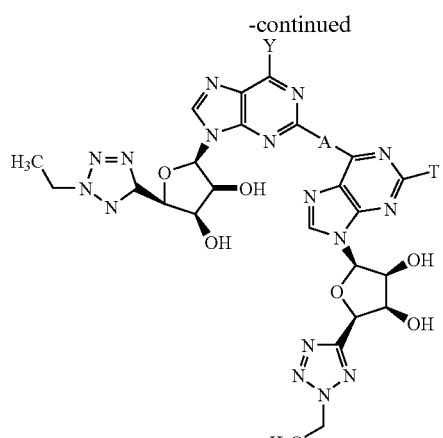

VII

Step 1:
Reaction of acetic acid (2R,5R)-4-acetoxy-2-(2,6-dichloro-purin-9-yl)-5-(2-ethyl-2H-tetrazol-5-yl)-tetrahydro-furan-3-yl ester (WO 98/28319) in DCE at 50° C. with the appropriate amine Y-H in the presence of DIPEA affords Intermediates RY.

Step 2:
Intermediates RY are deprotected using potassium carbonate in MeOH/chloroform at room temperature to yield Intermediates RY1.

Step 3:
Reaction of Intermediates RY1 individually with the appropriate Boc-protected amine (Boc)-A-H followed by deprotection in an analogous manner to that used in the preparation of Intermediate B gives the Intermediates RY1A Step 4:
Reaction of Intermediates RY1A individually with acetic acid (2R,5R)-4-acetoxy-2-(2,6-dichloro-purin-9-yl)-5-(2-ethyl-2H-tetrazol-5-yl)-tetrahydro-furan-3-yl ester (WO 98/28319) using conditions analogous to those described in Steps 1 and 2 affords the Intermediates RY1A2.

Step 5:
Intermediates RY1A2 are reacted in acetonitrile/N-methyl-pyrrolidone in the presence of sodium iodide, triethylamine, individually with the amines T-H. Heating with microwave radiation at temperatures from 120-220° C. gives the series of Examples of formula (VII).

Examples of the formula (VIII) are prepared as described below.

(VIII)

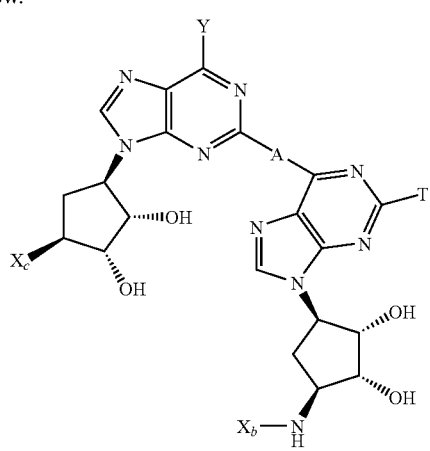

Scheme 4:

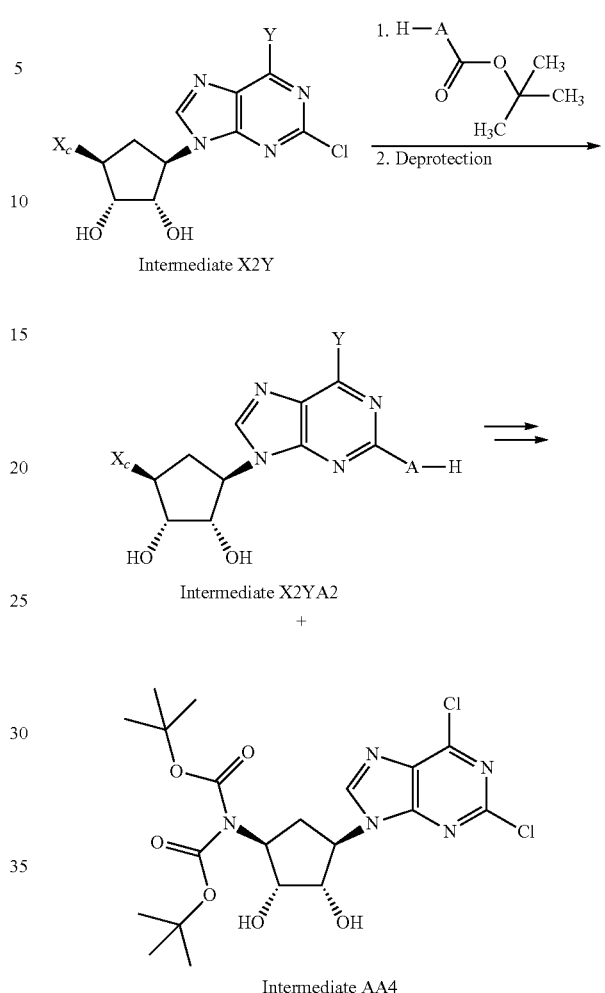

Intermediate X2Y

Intermediate X2YA2

+

Intermediate AA4

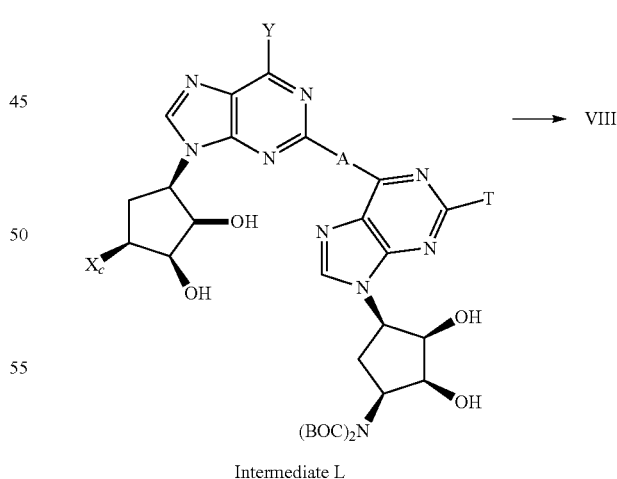

Intermediate L

These examples are prepared from Intermediates X2YA2 analogously to examples of formula (III). Intermediates X2YA2 are prepared from Intermediates X2Y in an analogous manner to that used in the preparation of Intermediate B by replacing (3R)-(+)-(3-Boc-amino)pyrrolidine with the appropriate Boc-protected amine (Boc)-A-H.

61
Boc-Protected Amine (Boc)-A-H:
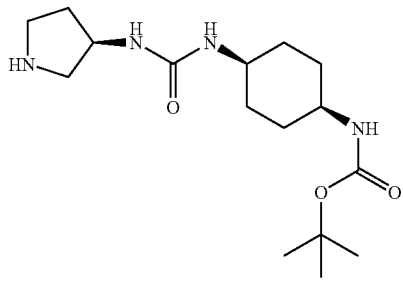
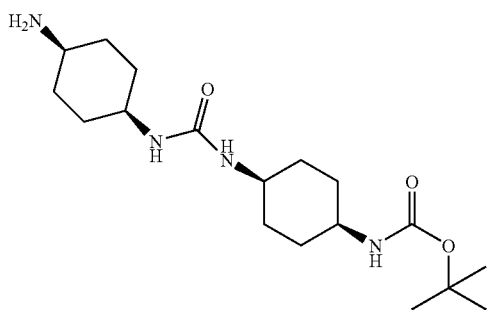
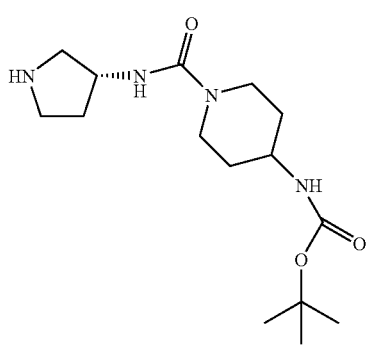
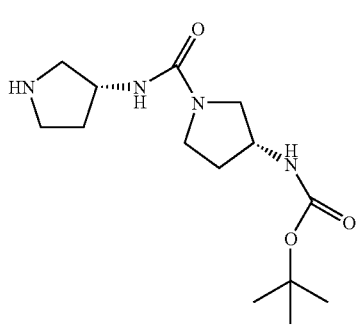
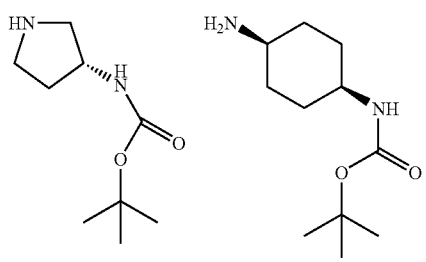
62
-continued
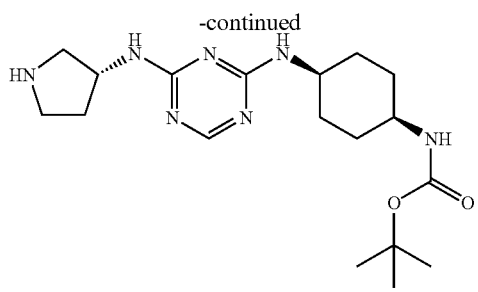
Resulting A Linkers:
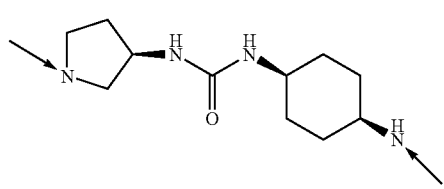
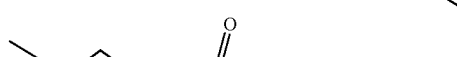
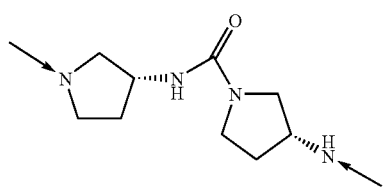
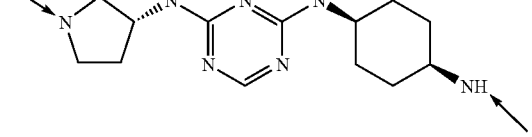
Intermediate L is converted to Example VIII in an analogues fashion to Example I.
Examples of the formula (IX) are prepared as described below.

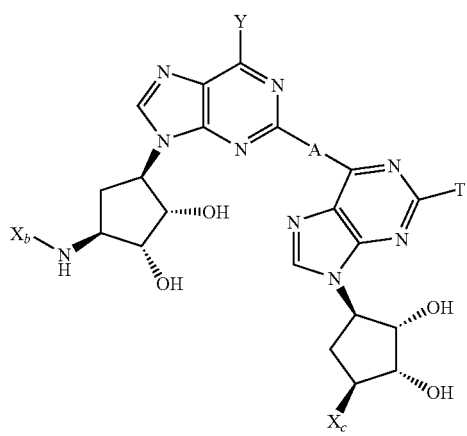

(IX)

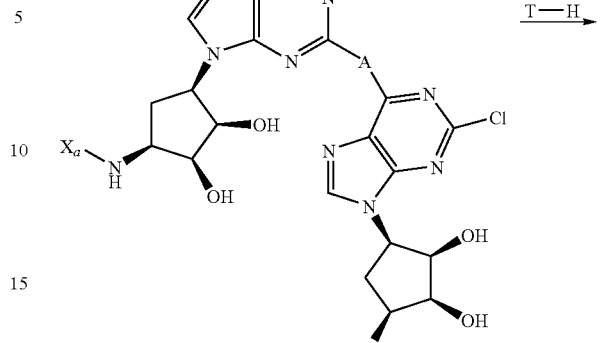

Intermediate M

Scheme 5:

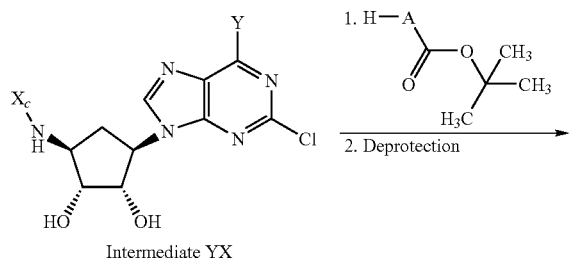

Intermediate YX

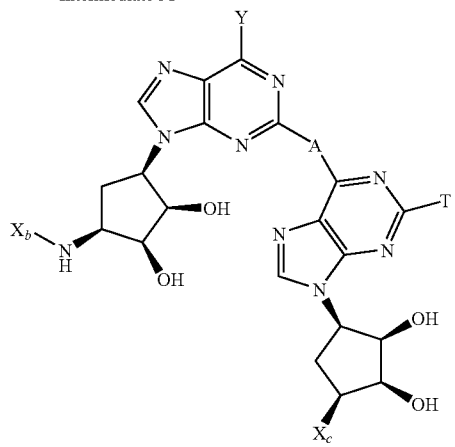

IX

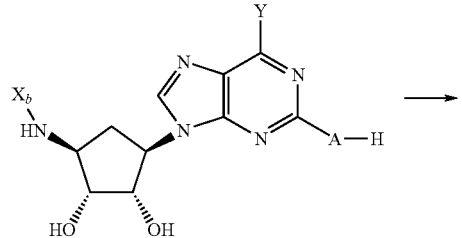

Intermediate YXBA2

+

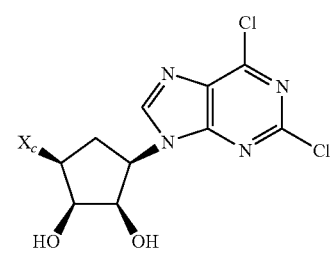

Intermediate X2A

These examples are prepared as follows:

Step 1: Intermediates YXBA2 are prepared from Intermediates YX in an analogous manner to that used in the preparation of Intermediate B by replacing (3R)-(+)-(3-Boc-amino)pyrrolidine with the appropriate Boc-protected amine (Boc)-A-H.

Step 2: Reaction of Intermediates YXBA2 in an analogous manner to that used to prepare [(1S,2R,3S,4R)-4-(2-chloro-6-{((R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-ylamino}-purin-9-yl)-2,3-dihydroxy-cyclopentyl]-di-carbamic acid tert-butyl ester (Example 1, Step 1), individually using the corresponding Intermediate X2A affords the Intermediates M.

Step 3: Intermediates M are reacted in acetonitrile/N-methyl-pyrrolidone in the presence of sodium iodide, triethylamine, individually with the amines T-H. Heating with microwave radiation at temperatures from 120-220° C. gives the series of Examples of formula (IX).

Boc-protected amine (Boc)-A-H, resulting A linkers and amines T-H are as described previously.

The invention claimed is:

1. A compound of formula (Ia), or stereoisomers or pharmaceutically acceptable salts thereof,

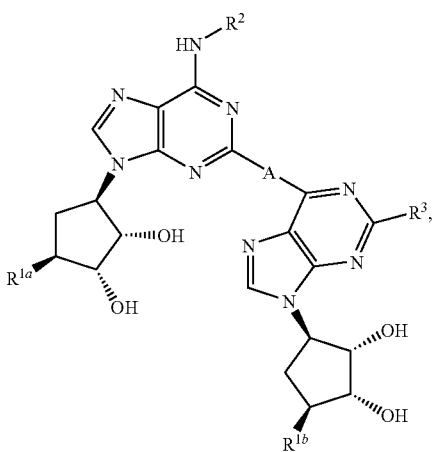

(Ia)

wherein
- $R^{1a}$ and $R^{1b}$ are independently selected from a 3- to 12-membered heterocyclic group containing from 1-4 ring nitrogen atoms and optionally containing from 1-4 other heteroatoms selected from the group consisting of oxygen and sulfur, that group being optionally substituted by oxo, O-$C_1$-$C_8$-alkyl, $C_6$-$C_{10}$-aryl, $R^{1c}$ or by $C_1$-$C_8$-alkyl optionally substituted by OH, or
- $R^{1a}$ and $R^{1b}$ are independently selected from —$NR^4R^4$, and —$NR^5$—$C_1$-$C_8$-alkylcarbonyl;
- $R^2$ is $C_1$-$C_8$-alkyl optionally substituted by OH, halogen $C_6$-$C_{10}$-aryl optionally substituted by OH, $SC_1$-$C_8$-alkyl, CN, halogen, O-$C_7$-$C_{14}$-aralkyl, or O-$C_1$-$C_8$-alkyl, a $C_3$-$C_{15}$-carbocyclic group optionally substituted by O—$C_7$-$C_{14}$ aralkyl, $C_3$-$C_{15}$-carbocyclic group, O—$C_1$-$C_8$-alkyl, $C_2$-$C_8$-alkenyl, $C_2$-$C_8$-alkynyl or $C_1$-$C_8$-alkyl, O—$C_1$-$C_8$-alkyl, —$SO_2$—$C_1$-$C_8$-alkyl, a 3- to 12-membered heterocyclic group containing from 1-4 ring nitrogen atoms and optionally containing from 1-4 other heteroatoms selected from the group consisting of oxygen and sulfur, that group being optionally substituted by 3- to 12-membered heterocyclic group containing from 1-4 ring nitrogen atoms and optionally containing from 1-4 other heteroatoms selected from the group consisting of oxygen and sulfur, $C_7$-$C_{14}$-aralkyl, or $C_6$-$C_{14}$-aryl optionally substituted by O—$C_7$-$C_{14}$-aralkyl, or
- $R^3$ is hydrogen, halo, $C_2$-$C_8$-alkenyl, $C_2$-$C_8$-alkynyl or $C_1$-$C_8$-alkoxycarbonyl, or
- $R^3$ is $C_1$-$C_8$-alkylamino optionally substituted by OH, $R^{3b}$, amino, di($C_1$-$C_8$-alkyl)amino, —NH—C(=O)—$C_1$-$C_8$-alkyl, —NH—$SO_2$—$C_1$-$C_8$-alkyl, —NH—C(=O)—NH—$R^{3c}$, —NH—C(=O)—NH—$C_1$-$C_8$-alkyl-$R^{3b}$, a $C_3$-$C_{15}$-carbocyclic group or by $C_6$-$C_{10}$-aryl optionally substituted by $C_6$-$C_{10}$-aryloxy, or
- $R^3$ is a 3- to 12-membered heterocyclic group containing from 1-4 ring nitrogen atoms and optionally containing from 1-4 other heteroatoms selected from the group consisting of oxygen and sulfur, that group being optionally substituted by 0-3$R^4$;
- $R^{3a}$ and $R^{3b}$ are each independently a 3- to 12-membered heterocyclic group containing at least one ring heteroatom selected from the group consisting of nitrogen, oxygen and sulfur; optionally substituted by halo, cyano, oxo, OH, carboxy, nitro, $C_1$-$C_8$-alkyl, $C_1$-$C_8$-alkylcarbonyl, OH—$C_1$-$C_8$-alkyl, $C_1$-$C_8$-haloalkyl, amino-$C_1$-$C_8$-alkyl, amino(OH)$C_1$-$C_8$-alkyl and $C_1$-$C_8$-alkoxy optionally substituted by aminocarbonyl;
- $R^{3c}$ is a 5- or 6-membered heterocyclic group containing at least one ring heteroatom selected from the group consisting of nitrogen, oxygen and sulfur, which is optionally substituted by a 5- or 6-membered heterocyclic group containing at least one ring heteroatom selected from the group consisting of nitrogen, oxygen and sulfur;
- $R^{3d}$ are independently a 5- or 6-membered heterocyclic ring containing at least one ring heteroatom selected from the group consisting of nitrogen, oxygen and sulfur, said 5- or 6-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl, $C_1$-$C_8$-alkoxy optionally substituted by aminocarbonyl, or a 5- or 6-membered heterocyclic ring containing at least one ring heteroatom selected from the group consisting of nitrogen, oxygen and sulfur, said ring also being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl, or $C_1$-$C_8$-alkoxy optionally substituted by aminocarbonyl;
- $R^4$ is selected from OH, $C_1$-$C_8$-alkyl optionally substituted by OH, $C_1$-$C_8$-alkoxy, $C_7$-$C_{14}$-aralkyl optionally substituted with OH, O-$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O-$C_1$-$C_8$-alkyl or -halogen, O-$C_6$-$C_{10}$-aryl optionally substituted by OH, $C_1$-$C_8$-alkyl, O-$C_1$-$C_8$-alkyl or -halogen, and $NR^{4f}C(O)NR^{4g}R^{4h}$;
- $R^{4f}$, $R^{4h}$ are, independently, H, or $C_1$-$C_8$-alkyl;
- $R^{4g}$ is a 3- to 12-membered heterocyclic group containing at least one ring heteroatom selected from the group consisting of nitrogen, oxygen and sulphur; and
- A is selected from

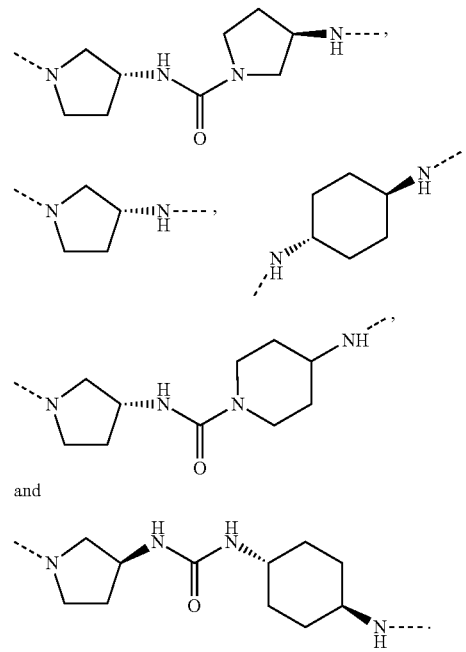

and

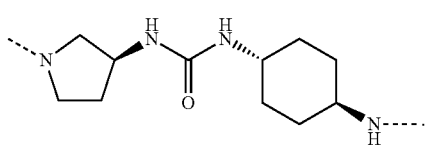

2. The compound according to claim 1 or pharmaceutically acceptable salts thereof selected from

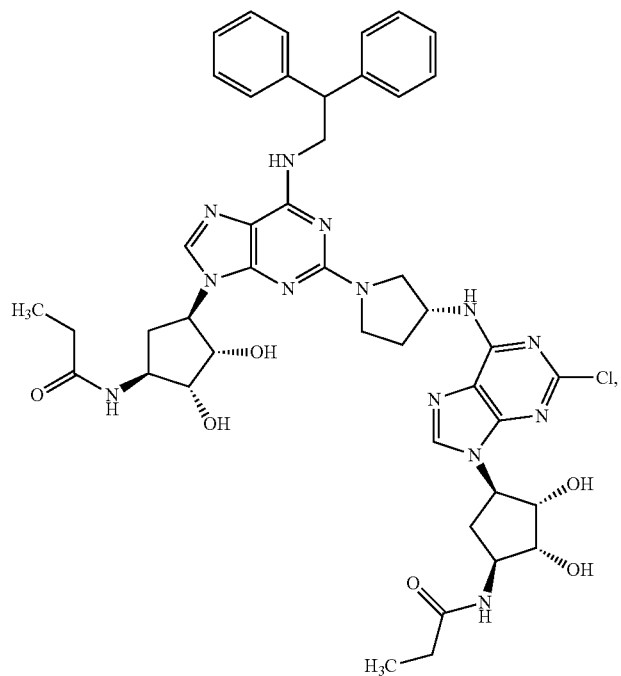
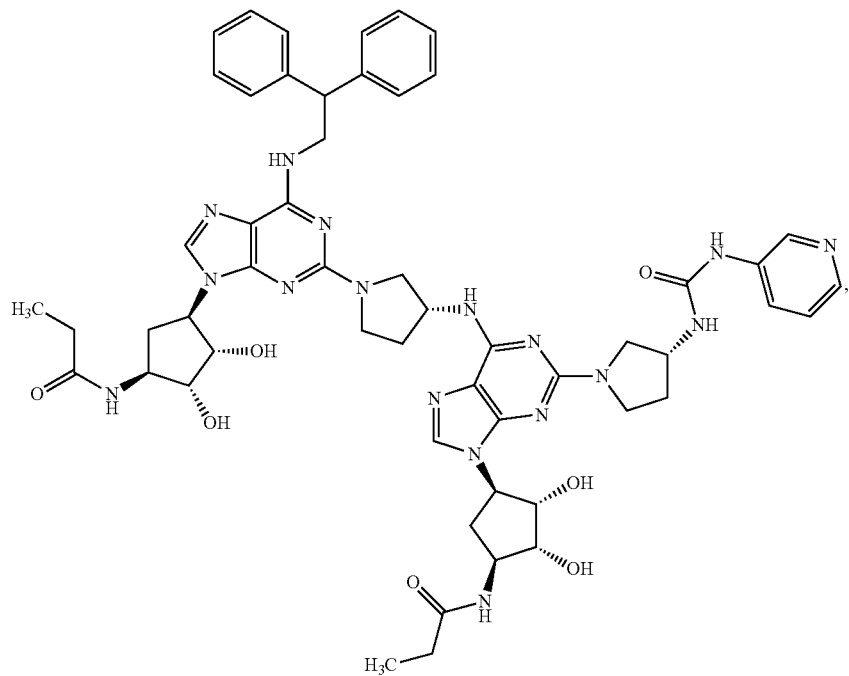

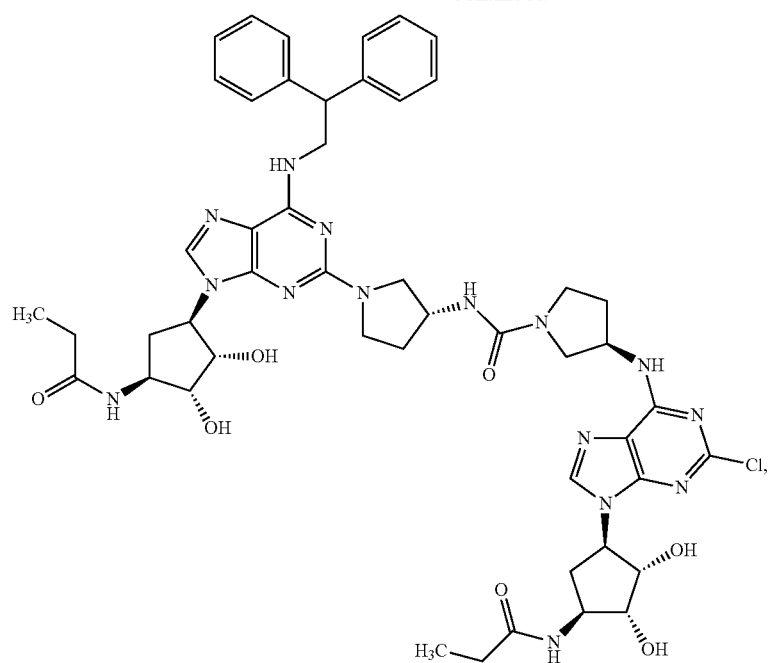
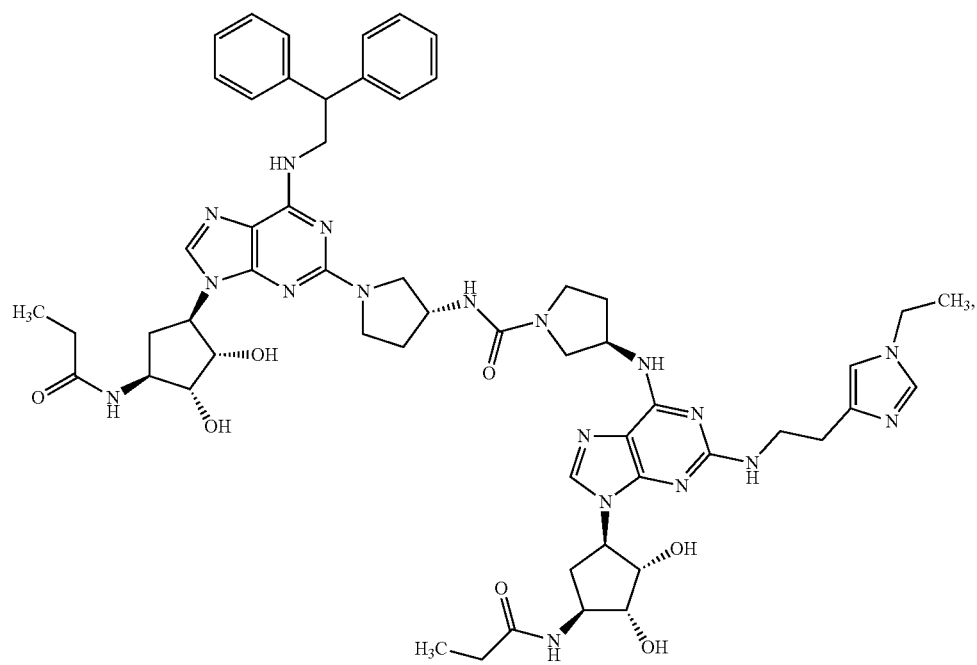

-continued

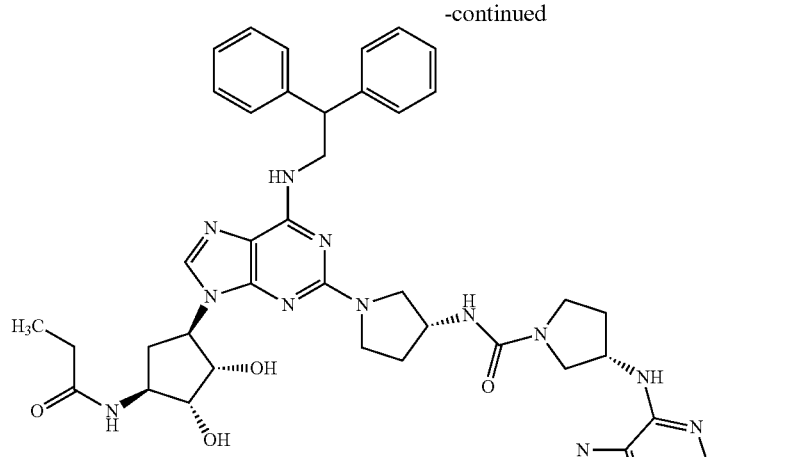

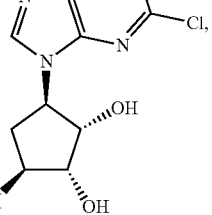
and

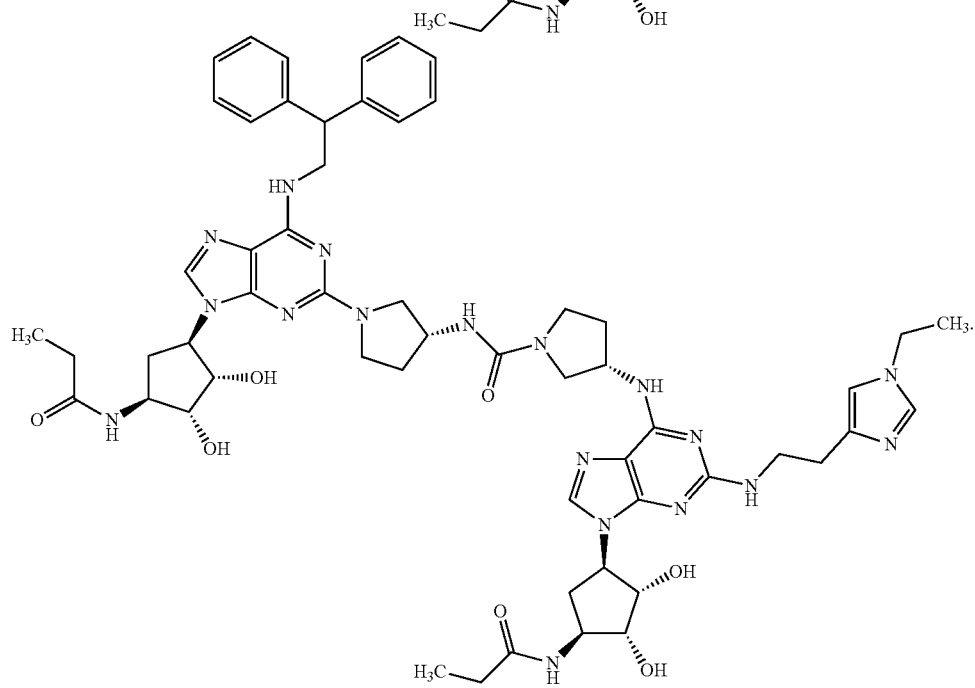

3. A pharmaceutical combination, comprising:
the compound according to claim 1 and
a second drug substance, wherein said drug substance is an anti-inflammatory, bronchodilatory, anti-histamine or anti-tussive drug substance, said compound and said drug substance being in the same or different pharmaceutical composition.

4. A pharmaceutical composition, comprising:
the compound according to claim 1, and
a pharmaceutically acceptable diluent or carrier.

* * * * *